US012638381B2

(12) United States Patent     (10) Patent No.: US 12,638,381 B2

Naveena-Chandran et al.     (45) Date of Patent:    May 26, 2026

(54) DETERMINING ION CONCENTRATION THROUGH DOWNHOLE OPTICAL SPECTROSCOPY

(71) Applicant: Halliburton Energy Services, Inc., Houston, TX (US)

(72) Inventors: Rohin Naveena-Chandran, Houston, TX (US); James Martin Price, Houston, TX (US); Bin Dai, Katy, TX (US); Syed Muhammad Farrukh Hamza, Houston, TX (US); Vinay K. Mishra, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 384 days.

(21) Appl. No.: 18/221,011

(22) Filed: Jul. 12, 2023

(65) Prior Publication Data

US 2024/0151637 A1     May 9, 2024

Related U.S. Application Data

(60) Provisional application No. 63/423,143, filed on Nov. 7, 2022.

(51) Int. Cl.
*G01N 21/31*     (2006.01)
*E21B 49/10*     (2006.01)
*G01N 33/28*     (2006.01)

(52) U.S. Cl.
CPC ............. *G01N 21/31* (2013.01); *E21B 49/10* (2013.01); *G01N 33/2823* (2013.01)

(58) Field of Classification Search
CPC .... G01N 21/31; G01N 33/2823; E21B 49/10; E21B 49/109
See application file for complete search history.

(56) References Cited

U.S. PATENT DOCUMENTS

2008/0314139 A1* 12/2008 DiFoggio ................ E21B 49/10
                                       73/152.55
2016/0282367 A1* 9/2016 Heinecke ................. C12Q 1/26
(Continued)

FOREIGN PATENT DOCUMENTS

WO      2006063094 A1    6/2006

OTHER PUBLICATIONS

Naveena-Chandran, et al., Resolving Chloride Ion Concentration through In-Situ Optical Spectroscopy: A Venture into Downhole Water chemistry analysis, SPWLA 64th Annual Logging Symposium, Jun. 10-14, 2023.

(Continued)

*Primary Examiner* — Michael J Dalbo
*Assistant Examiner* — Kaleria Knox
(74) *Attorney, Agent, or Firm* — John Wustenberg; C. Tumey Law Group PLLC

(57) ABSTRACT

Methods and systems for determining one or more ion components. The method may include disposing a fluid sampling tool into a wellbore wherein the fluid sampling tool includes at least one probe to fluidly connect the fluid sampling tool to a formation in the wellbore, and at least one passageway that passes through the at least one probe and into the fluid sampling tool. The method may further comprise drawing a formation fluid, as a fluid sample, through the at least one probe and through the at least one passageway, and analyzing the fluid sample in the fluid sampling tool for one or more ion components.

20 Claims, 13 Drawing Sheets

(56) References Cited

U.S. PATENT DOCUMENTS

2019/0096659 A1*  3/2019  Xu ....................... G06N 3/0464
2019/0360332 A1*  11/2019  Dai .......................... G06N 3/09

OTHER PUBLICATIONS

International Search Report and Written Opinion for International Patent Application No. PCT/US2023/029253 dated Nov. 21, 2023. PDF file. 10 pages.

* cited by examiner

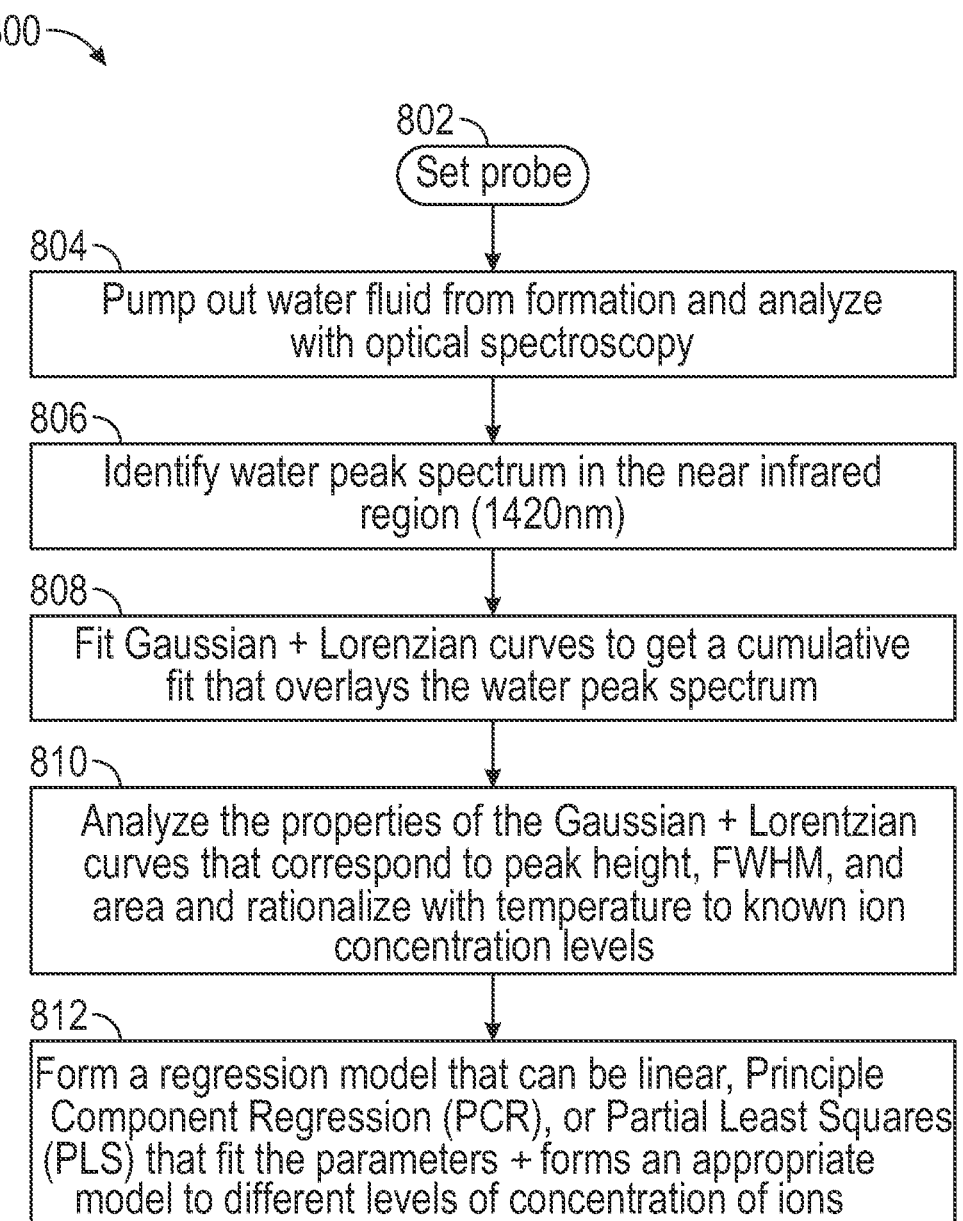

800

802 — Set probe

804 — Pump out water fluid from formation and analyze with optical spectroscopy

806 — Identify water peak spectrum in the near infrared region (1420nm)

808 — Fit Gaussian + Lorenzian curves to get a cumulative fit that overlays the water peak spectrum 810 — Analyze the properties of the Gaussian + Lorentzian curves that correspond to peak height, FWHM, and area and rationalize with temperature to known ion concentration levels 812 — Form a regression model that can be linear, Principle Component Regression (PCR), or Partial Least Squares (PLS) that fit the parameters + forms an appropriate model to different levels of concentration of ions

FIG. 8

DETERMINING ION CONCENTRATION THROUGH DOWNHOLE OPTICAL SPECTROSCOPY

BACKGROUND

During oil and gas exploration, many types of information may be collected and analyzed. The information may be used to determine the quantity and quality of hydrocarbons in a reservoir and to develop or modify strategies for hydrocarbon production. For instance, the information may be used for reservoir evaluation, flow assurance, reservoir stimulation, facility enhancement, production enhancement strategies, and reserve estimation. One technique for collecting relevant information involves obtaining and analyzing fluid samples from a reservoir of interest. There are a variety of different tools that may be used to obtain the fluid sample. The fluid sample may then be analyzed to determine fluid properties.

Conventional analysis has required transfer of fluid samples to a laboratory for analysis. Certain disadvantages are associated with such methods including the incursion of unwanted delays and representational inaccuracies. Once sampled, characterization of such fluids by these methods is met with additional challenges. For example, it is difficult to accurately ascertain fluid properties of a single water type in a sample when the sample is a mixture of many water types each derived from a different source (e.g., formation water, injected water, disposal water, mud filtrate).

Currently there is a challenge of resolving water chemistry outputs performing downhole fluid analysis. Current technology may distinguish various properties of hydrocarbons (oil and gas) and may have an indicator (by percentage or resistivity) of water but does not investigate concentrations of different ions (anions and cations) that make up water chemistry. Water chemistry plays an important role in the production of oil and gas reservoirs. The understanding of reservoir water properties is critical in determining field development facilities capable of handling produced water as either disposal, injection, or treatment. Further, water chemistry helps in understanding reservoirs connectivity, optimizing oil production, and in the monitoring of carbon capture and storage.

BRIEF DESCRIPTION OF THE DRAWINGS

These drawings illustrate certain aspects of some of the embodiments of the present disclosure, and should not be used to limit or define the disclosure:

FIG. 8 is a workflow in accordance with certain embodiments;

DETAILED DESCRIPTION

Figure 1:
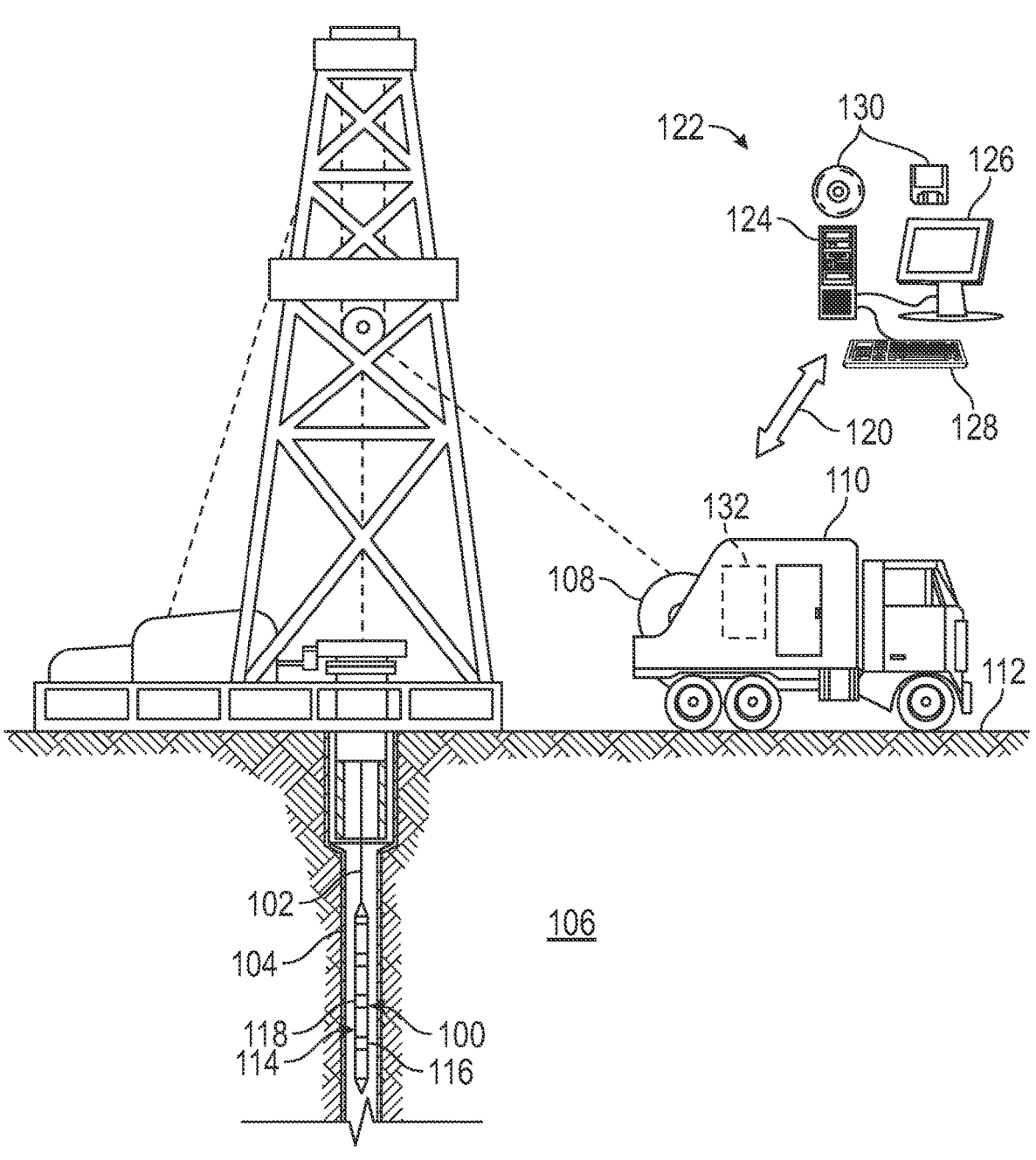
FIG. 1 is a schematic diagram of an example of a fluid sampling tool on a wireline.

Disclosed herein are methods and systems for sampling reservoir water and, more particularly, disclosed are methods and systems for performing downhole fluid analysis of water. Methodologies in accordance with the present disclosure use a downhole spectroscopy device with a fluid sampling device to determine concentration of ions. An optical spectrum in a near infrared region corresponding to water (1420 nm) may be split into at least two components using spectral deconvolution. Equations that may be used to carry out the spectral deconvolution include Gaussian, Lorentzian or Voight Curve with Gaussian and Lorentzian addition. Once this spectrum has been split (deconvolved), there are unique characteristics of the Gaussian and Lorentzian curves that correspond to different concentrations of ions. These are either or a combination of: peak height, Full Width Half Max (FWHM), or the Integrated Area of a component. By using these components in combination with temperature, a separate equation (model) may be realized which may be used to calculate ion concentration.

In some embodiments, water chemistry is quantified by measuring the bond strength of hydrogen bonded water, which shows distinguishable characteristics in Near Infrared (NIR) spectra depending upon its ionic environment. Variation in absorption intensity is due to the variation in the concentration of water and the variation in ion-dipole interactions between water molecules and other ions that exist in solution, such as sodium ($Na^+$) and chloride ($Cl^-$) ions for instance. A downhole optical sensor consisting of multiple broad bandpass filters, based on compressive sensing (CS) principle, termed integrated characterization section (ICS), was developed as fluid identification sensor for wireline formation tester. The compressive sensing based optical sensor uses several broadband filters as sensing matrix, instead of narrowband filters, and obtains high resolution optical spectrum of measured fluid via a compressive sensing reconstruction algorithm and a fluid spectral database.

As the term "compressive sensing" indicates, the number of multiplex spectral measurements (or number of optical filters, M) is much smaller than the dimension of the unknown spectrum (N) that is sought to recover. Because the number of measurements (M) is less than the number of unknown spectra (N), this is an underdetermined linear system. To find a solution, compressive sensing relies on the assumption that the spectral signal $f(\lambda)$ (transmission spectrum) or transformed spectral signal (absorption spectrum)

can be sparsely represented by a few basis functions in spectral domain. In mathematic term, the $i^{th}$ measurement of light intensity ($s_i$) can be described as Equation 1:

$$s_i = \int f(\lambda) \cdot t_i(\lambda) d\lambda \qquad \text{Equation 1}$$

where $f(\lambda)$ is an unknown spectral signal (transmission) light and $t_i(\lambda)$ represents the spectral response of the entire optical train for $i^{th}$ filter. It can be written as $t_i(\lambda) = L(\lambda) \cdot \phi_i(\lambda)$, where $L(\lambda)$ is the convolved spectral profile of optical sensor system (light source spectral profile, optical path spectral profile and detector spectral response profile) except the optical filter, and $\phi_i(\lambda)$ is the transmission spectrum $i^{th}$ optical filter. Both $L(\lambda)$ and $\phi_i(\lambda)$ are known profiles that can be characterized (pre-measured) for the sensor. The detector's measured signal $s_i$ can be treated as a transformation of the unknown signal $f(\lambda)$ by a known transfer function $t_i(\lambda)$. The recovery of signal $f(\lambda)$ is done through an inverse transformation of measured signal $s_i$. For a narrow band filter spectrometer, the filters separate lights into different wavelength regions. By measuring the intensity of transmitted light at each discrete wavelength window ($\lambda$), the spectrum can be obtained directly without the inversion. For broadband filters bases compressive sensing spectrometer, a compressive sensing-based signal inversion algorithm is needed to recover the fluid spectral signal $f(\lambda)$. In compressive sensing, the set of multiplex spectral measurements $s_i$, $i = 1, 2, \ldots, M$ is the result of projecting the input unknown spectral signal over a set of different modulating function $\phi_i(\phi)$, which represents the sensing matrix.

The basis functions can be obtained by Principal Component Analysis (PCA) decomposition of a spectral library. By analyzing an optical absorbance spectral database of large number of downhole water fluid with various level of ions such as chloride ions for instance, more than 99% of spectral variation can be explained by the first two principal components (PC). These two principal components are used as basis function for compression sensing inversion. With basis function established in absorbance space, Equation 1 can be inversed to recover $f(\lambda)$. Because $f(\lambda)$ represents the transmission spectrum of fluid sample, to use the principal component analysis basis function derived from absorbance space, a simple absorbance to transmission transformation is performed.

$$f(\lambda) = 10^{-g(\lambda)} \qquad \text{Equation 2}$$

where $g(\lambda)$ is the absorbance spectrum. It can be approximated by linear combination of those 2 principal component analysis basis functions in addition to the mean spectra:

$$g(\lambda) = \sum_{j=1}^{3} \beta_j * PC_j + m \qquad \text{Equation 3}$$

where $\beta_j$ is an unknown weighting coefficients and m is the mean spectrum of database spectra.

Combining the equations above, Equation 1 becomes:

$$s_i = \int 10^{-\left(\sum_{j=1}^{3} \beta_j * PC_j + m\right)} \cdot t_i(\lambda) d\lambda \qquad \text{Equation 4}$$

where $i = 1, 2, \ldots, 25$

With twenty-five broadband filters and the corresponding twenty-five measurements of sensor responses ($s_i$), the two unknowns ($\beta_j$ weighting coefficients) can be estimated by solving twenty-five nonlinear equations. The previous underdetermined linear equation system (Equation 1) is thus transformed to an overdetermined nonlinear equation system (Equation 4). The $\beta_j$ weighting coefficients can be obtained by solving Equation 4 using a constrained optimization algorithm (LBFGS-B optimization algorithm from the Python Scipy "optimize" library), with the resulting spectra being nonnegatively constrained.

Depending upon the chemical element within the mixture, the absorption spectrum can be represented by one or more mathematical functions. The following Equation 5 shows a general formula for a Gaussian function:

$$G(\lambda) = \alpha \cdot e^{-\frac{(\lambda - \lambda_0)^2}{2\sigma^2}} \qquad \text{Equation 5}$$

where $\alpha$ is the height of the Gaussian, $\lambda_0$ is the central wavelength, and $\sigma$ is the Full Width Half Maximum (FWHM) of the function.

The Absorption spectrum is constructed through a combination of decomposed (deconvolved) Gaussian spectra that additively fit the shape of the respective spectrum:

$$A(\lambda) = \sum_{m=1} G(\lambda_m) \qquad \text{Equation 6}$$

where m is the center wavelength of that form that deconvolved Gaussian curve.

Without any peak fitting or spectral decomposition, clear trends may be observed with peak broadening (full width half maximum, FWHM) and center peak position decreasing with increasing ion concentration in water, such as chloride and/or sodium for instance. Sensitivity to less than 1% change in sodium and chloride content is visibly discernable from laboratory spectra. A three component Gaussian fit may be performed for each spectrum to isolate more accurately each ionic contribution, such as to quantify the chloride and/or sodium perturbations on the water absorbance peak. The Gaussian decomposition may be represented by optimizing a variation of equation to minimize the residuals of the fitted variables to the laboratory spectra.

Downhole sampling of a reservoir fluid may be performed to carry out certain embodiments of the present disclosure. Generally speaking, downhole sampling refers to a type of downhole operation, which may be used for formation evaluation, asset decisions, and operational decisions. In general, a fluid sampling tool is utilized for analyzing the fluids from a formation and their composition. Water sampling is often not a priority or performed. Additionally, if water sampling is performed, the water sample is analyzed at a lab at surface. Methods and systems discussed below may allow for water sampling to be performed downhole, to perform in-situ analysis of fluid and ionic properties of samples, and to distinguish between different water types.

As disclosed herein, a property of a fluid refers to a chemical property, phase property, i.e., fluid (liquid aqueous, liquid organic, or gas), or solid phase in concentration or identification, or phase behavior. Examples of properties may include, compositional component concentrations, such as methane, ethane, propane, butane, and pentane; organic liquid components, such as a hexane plus (C6+) fraction or hydrocarbon components therein, saturates fraction, aromatics fraction, resins fraction, asphaltenes fraction; total acid number; pH, eH (activity of electrons), water composition, including cations such as sodium, potassium, calcium, magnesium and trace cations, anions such as chloride, bromide, sulfide, sulfate, carbonate, bicarbonate, other dissolved solids; organic acids and/or their conjugates; and other inorganic components such as carbon dioxide, hydrogen sulfide, nitrogen or water. Physical properties may include compressibility, density, thermal conductivity, heat capacity, viscosity; phase behavior including bubble point, gas to oil ratio, phase envelope for gas-liquid or solid-liquid, including asphaltenes or waxes; and compositional grading with depth. Properties may also include the interpretation of similarity or differences between different set fluids such as that reflected by reservoir or field architecture, and reservoir compartmentalization. Properties may be used therein to obtain reservoir or field architecture or reservoir compartmentalization, compositional grading, and may be used to interpreted processes leading to various compositional grading or other equilibrium or disequilibrium distributions of fluids and fluid properties. Properties may therefore refer to the measured, calculated, and inferred properties obtained from sensor measurements and the properties derived from other therein such as but not limited to that by interpretation, such as equation of state interpretation.

For example, the methods and apparatus disclosed herein may identify the phases of each dominating fluid for each channel. The methods and apparatus disclosed herein may further identify pure phase channel observations versus mixed phase channel observations. Identifying the fluid type or fluid phase on a per channel basis may further benefit the estimation of fluid phase ratios or concentrations; the assessment of mud contamination; the construction of pure signature for the formation fluids; and the producible water cut of a zone, including, but not limited to, a transition zone in which both formation oil and formation water is simultaneously sampled.

A method of fluid identification may comprise clustering a plurality of channels to automatically classify an observed optical or non-optical spectrum into different fluid groups. The methods may also comprise fluid labeling of each of the fluid groups, wherein the fluid labeling may be guided by the observation of a deterministic or probabilistic sensor channel which responds characteristically to different phases such as density sensor channel observations. After completion of the fluid labeling step, a fluid ratio estimation and a fluid signature extraction may be determined. Fluid ratio estimation and fluid signature estimation may be determined or extracted by grouping such as but not limited to clustering and labeling fluids based on the characteristic channel observation such as but not limited to the density observation.

Conventional methods may depend on pre-processing of the observed channel responses such as but not limited to optical data responses, such as debiasing and normalization. By contrast, the grouping methods such as but not limited to clustering methods disclosed herein may depend on a distribution such as a statistical distribution, rather than exclusively an amplitude bias or scaling as in conventional methods. The grouping methods such as clustering methods disclosed herein present a more robust method for fluid identification. The fluid labeling method disclosed herein may improve fluid classification performance by sharing information between at least two paired channels of at least one sensor. Cross sensor channel paring is also possible. Moreover, the fluid labeling methods disclosed herein may improve the accuracy of channel pairs of low separability by importing guiding information such as observed density, capacitance, resistivity, and acoustic information.

During formation tester pump outs, reservoir fluids are often multi-phase flow including slug flow, dispersed flow, and emulsion flow, which may present difficulties in measuring combinations of liquids (water and oil) and gases or in some cases solids as well. It may be desirable to measure the physical and chemical properties of the individual phases of the fluids. The reservoir fluid compositions and distributions provide information for field engineers to make decisions on field development. Accurate gas composition may also assist in decision making regarding the installation of expensive production facilities. By directly measuring the sensor responses such as light-absorption responses for optical sensors of compositions in fluid samples, for instance optical measurement may provide an approach for fluid identification, composition analysis, and physical and chemical properties analysis.

The fluid samples may be measured either in a laboratory environment or in a real time subsurface borehole. Downhole fluid samples need not be captured in a container for analysis. Hence, as disclosed herein, the subsurface sensor channel measurements may be embodied by optical spectroscopy channels and a density sensor channel, but the embodiment is not exclusive to these sensors or channels. Optical sensor channel analysis may provide real-time information fluids at the field subsurface pressure and temperature. Other sensors with at least one channel include resistivity sensors, capacitance sensors, acoustic sensors, chromatographic sensors, microfluidic sensors, phase behavior sensors including but not limited to compressibility sensors and bubble point sensors, electrochemical sensors, mass spectrometer or mass spectroscopy sensors. Additionally, in the field the reservoir compositional variations may be directly mapped with greater spatial resolution than may otherwise be available, based on the number of samples which may be acquired downhole and sent to a laboratory. An in-situ compositional analysis may be combined with a spatial mapping of compositional properties and may provide an improved basis for selecting the locations from which to sample fluids for laboratory analysis. Moreover, the sample quality, as it is being withdrawn from a reservoir, may be quantified in terms of aliquot representation of the formation fluid in the reservoir and contamination levels of drilling fluid filtrate.

In some embodiments, it should be noted that only limited sensor channels such as optical channels may be implemented in subsurface optical spectroscopy. For example, the optical spectra of fluid samples may be measured channel by channel dynamically. In other examples, multiple channels may be acquired simultaneously, but at different locations. In other examples, a viewing window of the channels may oscillate between phases or a combination of phases therein and may provide difficult temporal analysis of the fluid's physical and chemical behavior.

For example, the fluid's chemical behavior may include, but may not limited to, a petroleum composition comprising saturates, aromatics, resins, asphaltenes fractions, methane, ethane, propane, butane, pentane, hexane and higher components and individual or lumped higher hydrocarbon components (where lumping may be the composite analysis or reporting of two or more hydrocarbon components), inorganic component composition, including water, nitrogen, carbon dioxide, and hydrogen sulfide chemical potential, including, but not limited to, reactive capability acidic levels of individual components, i.e., organic acids, or as a whole, i.e., pH or total acid number (TAN), or for instance redox potential. These chemical properties may be directly probed optically, by optical analysis in combination with other measurement devices, which may include, but may not be limited to, density, bubble point, compressibility, acoustic, NMR, capacitance, dielectric spectroscopy, nuclear methods, x-ray methods, terahertz methods, and resistivity.

Alternatively, chemical properties may be interpreted based on physical, chemical, or empirical models as a secondary interpretation based on the directly probed chemical properties, which may include but may not be limited to the listed methods. For example, physical properties may include, but may not be limited to, bubble point, compressibility, phase envelope, density, and viscosity, and may be measured directly by devices such as density sensors, viscometers, phase behavior experimentation, trapped volume devices, fractionation devices such as valved devices or membrane devices or derived by physical, chemical, or empirical models as a secondary interpretation based on directly probed physical properties. Physical properties may be measured or derived based, in part, on multiple measurements. As a non-limiting example for instance, phase behavior (or other physical properties), like compressibility or bubble point may be derived based on combinations of physical measurements and compositions as modeled by an equation of state (EOS) such as, but not limited to, as Peng Robertson or SRK cubic equation of state, a viral equation of state, or a PC-SAFT equation of state or an empirical machine learning model such as, but not limited to a neural network or a random forest model or a gradient boost method. Multiphase fluids provide difficulties for interpretation.

During a subsurface optical measurement, sampled formation fluids may be together with some single phase or multiphase mud contaminations, flow through the sampling path. Alternatively, multiphase fluids may flow through the sampling path directly from multiphase formation fluids. Alternatively, multiphase fluids may be induced from phase changes due to pressure, volume, or temperature perturbations during sampling. In some examples, the sampled fluids for different channels may be distributed in space or time, such as channels configured in a rotating wheel positioned in an optical path of a fluid phase detector. However, as disclosed herein, the fluids may be sampled temporally by using a rotating wheel, wherein the fluids may be assumed to be the same phase (single-phase assumption). Consequently, obtaining the pure signature for the formation fluids and the mud filtrate may prove problematic, yielding errors for water/hydrocarbon ratio estimation and mud contamination assessment.

The present disclosure provides methods and apparatus for identifying the phases of dominating fluid for each channel, and further for identifying pure phase channel observations versus mixed phase channel observations. Identifying the fluid type on a per channel basis may further benefit the following: a) the estimation of fluid phase ratios or concentrations; b) the assessment of mud contamination; c) the construction of pure signature for the formation fluids; d) the producible water cut of a zone, including but not limited to, a transition zone; and e) the measurement of fluid properties for at least one of the sample phases (oil, water, gas, solid).

In addition, the present disclosure provides methods and apparatus for performing downhole fluid analysis. Downhole fluid analysis based optical spectroscopy may be performed to distinguish between various water types (e.g., injected water, disposal water, formation water, mud filtrate) and to recognize ionic properties including ion concentrations. Furthermore, the methods and apparatus of the present disclosure may improve upon conventional practices by enabling diagnosis of water production and compatibility of a formation for salt water disposal and/or carbon capture and sequestration based on the analysis.

FIG. 1 is a schematic diagram of fluid sampling tool 100 on a conveyance 102. As illustrated, wellbore 104 may extend through subterranean formation 106. In examples, reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a hoist 108 may be used to run fluid sampling tool 100 into wellbore 104. Hoist 108 may be disposed on a vehicle 110. Hoist 108 may be used, for example, to raise and lower conveyance 102 in wellbore 104. While hoist 108 is shown on vehicle 110, it should be understood that conveyance 102 may alternatively be disposed from a hoist 108 that is installed at surface 112 instead of being located on vehicle 110. Fluid sampling tool 100 may be suspended in wellbore 104 on conveyance 102. Other conveyance types may be used for conveying fluid sampling tool 100 into wellbore 104, including coiled tubing and wired drill pipe, conventional drill pipe for example. Fluid sampling tool 100 may comprise a tool body 114, which may be elongated as shown on FIG. 1. Tool body 114 may be any suitable material, including without limitation titanium, stainless steel, alloys, plastic, combinations thereof, and the like. Fluid sampling tool 100 may further include one or more sensors 116 for measuring properties of the fluid sample, reservoir fluid, wellbore 104, subterranean formation 106, or the like. In examples, fluid sampling tool 100 may also include a fluid analysis module 118, which may be operable to process information regarding fluid sample, as described below. The fluid sampling tool 100 may be used to collect fluid samples from subterranean formation 106 and may obtain and separately store different fluid samples from subterranean formation 106.

In examples, fluid analysis module 118 may comprise at least one sensor that may continuously monitor a reservoir fluid. Such sensors include optical sensors, acoustic sensors, electromagnetic sensors, conductivity sensors, resistivity sensors, a capacitance sensor, selective electrodes, density sensors, mass sensors, thermal sensors, chromatography sensors, viscosity sensors, bubble point sensors, fluid compressibility sensors, flow rate sensors. Sensors may measure a contrast between drilling fluid filtrate properties and formation fluid properties. Fluid analysis module 118 may be operable to derive properties and characterize the fluid sample. By way of example, fluid analysis module 118 may measure absorption, transmittance, or reflectance spectra and translate such measurements into component concentrations of the fluid sample, which may be lumped component concentrations, as described above. The fluid analysis module 118 may also measure gas-to-oil ratio, fluid composition, water cut, live fluid density, live fluid viscosity, formation pressure, and formation temperature. Fluid analysis module 118 may also be operable to determine fluid contamination of the fluid sample and may include any instrumentality or aggregate of instrumentalities operable to compute, classify, process, transmit, receive, retrieve, origi-nate, switch, store, display, manifest, detect, record, repro-duce, handle, or utilize any form of information, intelli-gence, or data for business, scientific, control, or other purposes. For example, fluid analysis module 118 may include random access memory (RAM), one or more pro-cessing units, such as a central processing unit (CPU), or hardware or software control logic, ROM, and/or other types of nonvolatile memory.

Any suitable technique may be used for transmitting phase signals from the fluid sampling tool 100 to the surface 112. As illustrated, a communication link 120 (which may be wired or wireless, for example) may be provided that may transmit data from fluid sampling tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. The information handling system 122 may act as a data acquisition system and possibly a data process-ing system that analyzes information from fluid sampling tool 100. For example, information handling system 122 may process the information from fluid sampling tool 100 for determination of fluid contamination. The information handling system 122 may also determine additional proper-ties of the fluid sample (or reservoir fluid), such as compo-nent concentrations, pressure-volume-temperature proper-ties (e.g., bubble point, phase envelop prediction, etc.) based on the fluid characterization. This processing may occur at surface 112 in real-time. Alternatively, the processing may occur downhole hole or at surface 112 or another location after recovery of fluid sampling tool 100 from wellbore 104. Alternatively, the processing may be performed by an infor-mation handling system in wellbore 104, such as fluid analysis module 118. The resultant fluid contamination and fluid properties may then be transmitted to surface 112, for example, in real-time.

Figure 2:
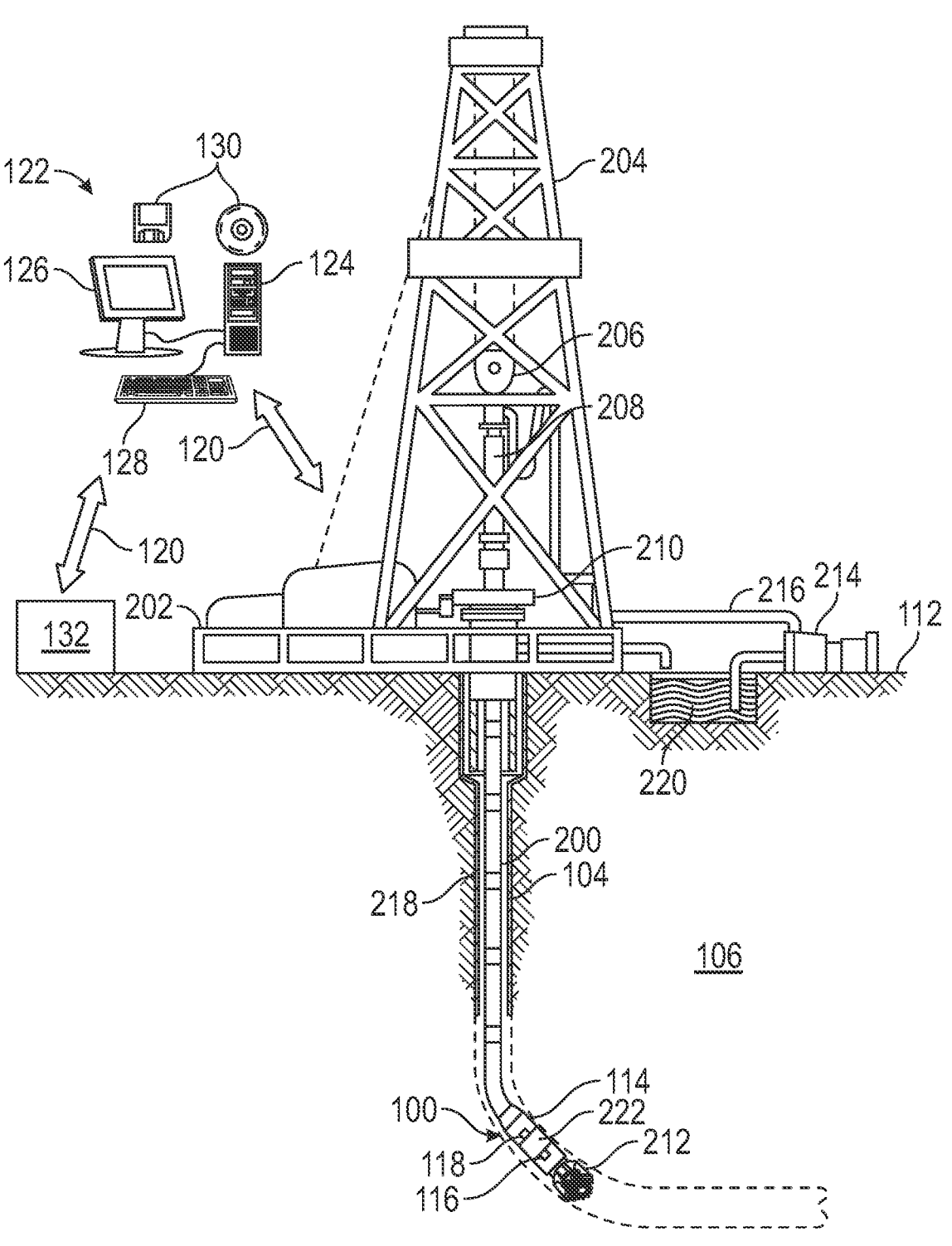
FIG. 2 is a schematic diagram of an example of the fluid sampling tool on a drill string.

Referring now to FIG. 2, a schematic diagram of fluid sampling tool 100 disposed on a drill string 200 in a drilling operation. Fluid sampling tool 100 may be used to obtain a fluid sample, for example, a fluid sample of a reservoir fluid from subterranean formation 106. The reservoir fluid may be contaminated with well fluid (e.g., drilling fluid) from well-bore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 2 shows a vertical or low inclination angle well, high inclination angle or horizontal placement of the well and equipment is also possible. It should further be noted that while FIG. 2 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 202 may support a derrick 204 having a traveling block 206 for raising and lowering drill string 200. Drill string 200 may include, but is not limited to, drill pipe and coiled tubing, as generally known to those skilled in the art. A kelly 208 may support drill string 200 as it may be lowered through a rotary table

210. A drill bit 212 may be attached to the distal end of drill string 200 and may be driven either by a downhole motor and/or via rotation of drill string 200 from the surface 112. Without limitation, drill bit 212 may comprise roller cone bits, PDC bits, natural diamond bits, any hole openers, reamers, coring bits, and the like. As drill bit 212 rotates, it may create and extend wellbore 104 that penetrates various subterranean formations 106. A pump 214 may circulate drilling fluid through a feed pipe 216 to kelly 208, downhole through interior of drill string 200, through orifices in drill bit 212, back to surface 112 via annulus 218 surrounding drill string 200, and into a retention pit 220.

Drill bit 212 may be just one piece of a downhole assembly that may include one or more drill collars 222 and fluid sampling tool 100. Fluid sampling tool 100, which may be built into the drill collars 222 may gather measurements and fluid samples as described herein. One or more of the drill collars 222 may form a tool body 114, which may be elongated as shown on FIG. 2. Tool body 114 may be any suitable material, including without limitation titanium, stainless steel, alloys, plastic, combinations thereof, and the like. Fluid sampling tool 100 may be similar in configuration and operation to fluid sampling tool 100 shown on FIG. 1 except that FIG. 2 shows fluid sampling tool 100 disposed on drill string 200. Alternatively, the sampling tool may be lowered into the wellbore after drilling operations on a wireline.

Fluid sampling tool 100 may further include one or more sensors 116 for measuring properties of the fluid sample reservoir fluid, wellbore 104, subterranean formation 106, or the like. The properties of the fluid are measured as the fluid passes from the formation through the tool and into either the wellbore or a sample container. As fluid is flushed in the near wellbore region by the mechanical pump, the fluid that passes through the tool generally reduces in drilling fluid filtrate content, and generally increases in formation fluid content. The fluid sampling tool 100 may be used to collect a fluid sample from subterranean formation 106 when the filtrate content has been determined to be sufficiently low. Sufficiently low depends on the purpose of sampling. For some laboratory testing below 10% drilling fluid contami-nation is sufficiently low, and for other testing below 1% drilling fluid filtrate contamination is sufficiently low. Suf-ficiently low also depends on the nature of the formation fluid such that lower requirements are generally needed, the lighter the oil as designated with either a higher GOR or a higher API gravity. Sufficiently low also depends on the rate of cleanup in a cost benefit analysis since longer pump out times utilized to incrementally reduce the contamination levels may have prohibitively large costs. As previously described, the fluid sample may comprise a reservoir fluid, which may be contaminated with a drilling fluid or drilling fluid filtrate. Fluid sampling tool 100 may obtain and sepa-rately store different fluid samples from subterranean for-mation 106 with fluid analysis module 118. Fluid analysis module 118 may operate and function in the same manner as described above. However, storing of the fluid samples in the fluid sampling tool 100 may be based on the determi-nation of the fluid contamination. For example, if the fluid contamination exceeds a tolerance, then the fluid sample may not be stored. If the fluid contamination is within a tolerance, then the fluid sample may be stored in fluid sampling tool 100.

As previously described, information from fluid sampling tool 100 may be transmitted to an information handling system 122, which may be located at surface 112. As illustrated, communication link 120 (which may be wired or wireless, for example) may be provided that may transmit data from fluid sampling tool 100 to an information handling system 111 at surface 112. Information handling system 140 may include a processing unit 124, a monitor 126, an input device 128 (e.g., keyboard, mouse, etc.), and/or computer media 130 (e.g., optical disks, magnetic disks) that may store code representative of the methods described herein. In addition to, or in place of processing at surface 112, processing may occur downhole (e.g., fluid analysis module 118). In examples, information handling system 122 may perform computations to estimate clean fluid composition.

Figure 3:
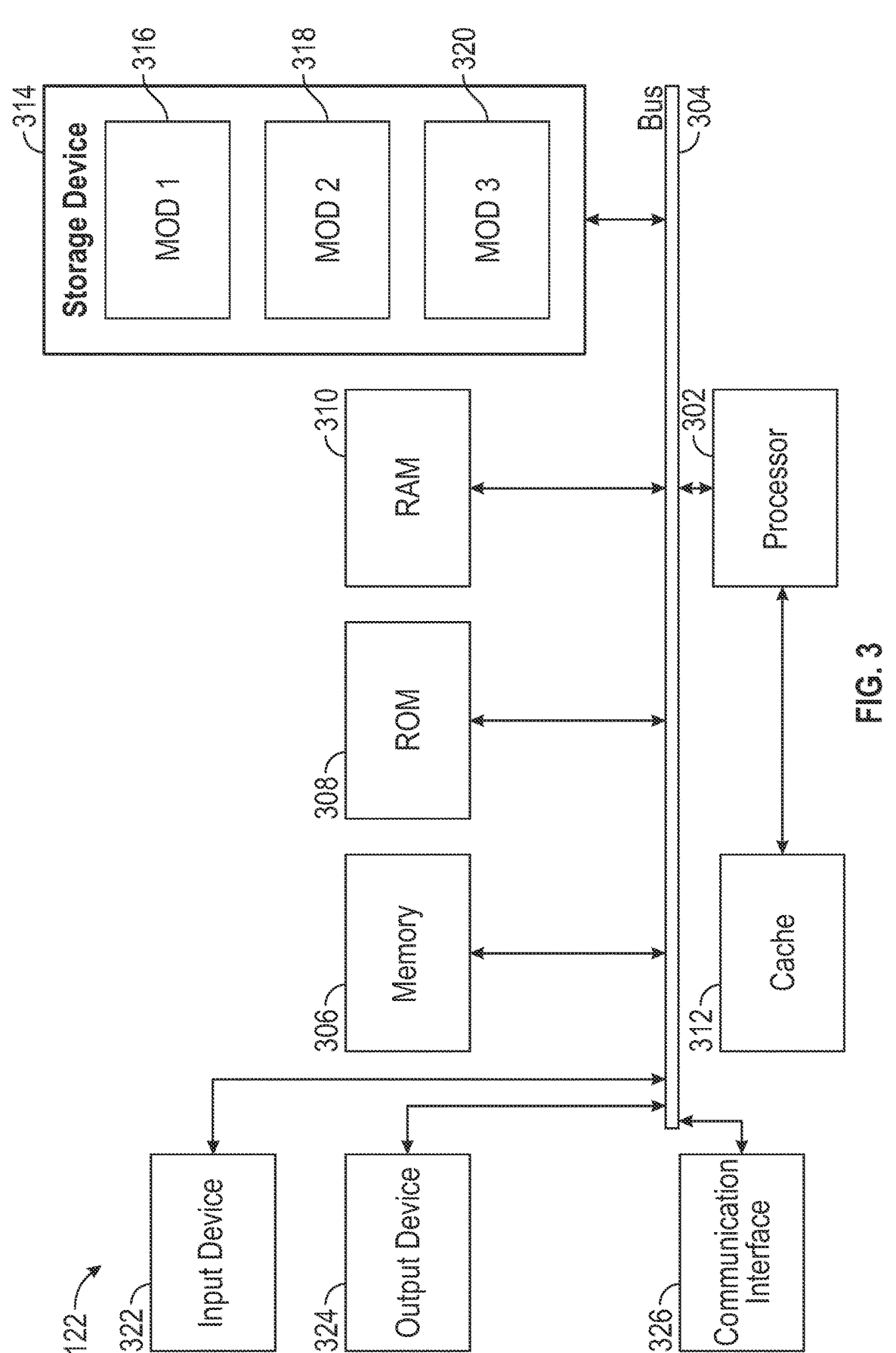
FIG. 3 is a schematic of an information handling system.

FIG. 3 illustrates information handling system 122 which may be employed to perform various blocks, methods, and techniques disclosed herein. As illustrated, information handling system 122 includes a processing unit (CPU or processor) 302 and a system bus 304 that couples various system components including system memory 306 such as read only memory (ROM) 308 and random-access memory (RAM) 310 to processor 302. Processors disclosed herein may all be forms of this processor 302. Information handling system 122 may include a cache 312 of high-speed memory connected directly with, in close proximity to, or integrated as part of processor 302. Information handling system 122 copies data from system memory 306 and/or storage device 314 to cache 312 for quick access by processor 302. In this way, cache 312 provides a performance boost that avoids processor 302 delays while waiting for data. These and other modules may control or be configured to control processor 302 to perform various operations or actions. Other system memory 306 may be available for use as well. System memory 306 may include multiple different types of memory with different performance characteristics. It may be appreciated that the disclosure may operate on information handling system 122 with more than one processor 302 or on a group or cluster of computing devices networked together to provide greater processing capability. Processor 302 may include any general-purpose processor and a hardware module or software module, such as first module 316, second module 318, and third module 320 stored in storage device 314, configured to control processor 302 as well as a special-purpose processor where software instructions are incorporated into processor 302. Processor 302 may be a self-contained computing system, containing multiple cores or processors, a bus, memory controller, cache, etc. A multi-core processor may be symmetric or asymmetric. Processor 302 may include multiple processors, such as a system having multiple, physically separate processors in different sockets, or a system having multiple processor cores on a single physical chip. Similarly, processor 302 may include multiple distributed processors located in multiple separate computing devices but working together such as via a communications network. Multiple processors or processor cores may share resources such as system memory 306 or cache 312 or may operate using independent resources. Processor 302 may include one or more state machines, an application specific integrated circuit (ASIC), or a programmable gate array (PGA) including a field PGA (FPGA).

Each individual component discussed above may be coupled to system bus 304, which may connect each and every individual component to each other. System bus 304 may be any of several types of bus structures including a memory bus or memory controller, a peripheral bus, and a local bus using any of a variety of bus architectures. A basic input/output (BIOS) stored in ROM 308 or the like, may provide the basic routine that helps to transfer information between elements within information handling system 122, such as during start-up. Information handling system 122 further includes storage devices 314 or computer-readable storage media such as a hard disk drive, a magnetic disk drive, an optical disk drive, tape drive, solid-state drive, RAM drive, removable storage devices, a redundant array of inexpensive disks (RAID), hybrid storage device, or the like. Storage device 314 may include software modules 316, 318, and 320 for controlling processor 302. Information handling system 122 may include other hardware or software modules. Storage device 314 is connected to the system bus 304 by a drive interface. The drives and the associated computer-readable storage devices provide nonvolatile storage of computer-readable instructions, data structures, program modules and other data for information handling system 122. In one aspect, a hardware module that performs a particular function includes the software component stored in a tangible computer-readable storage device in connection with the necessary hardware components, such as processor 302, system bus 304, and so forth, to carry out a particular function. In another aspect, the system may use a processor and computer-readable storage device to store instructions which, when executed by the processor, cause the processor to perform operations, a method or other specific actions. The basic components and appropriate variations may be modified depending on the type of device, such as whether information handling system 122 is a small, handheld computing device, a desktop computer, or a computer server. When processor 302 executes instructions to perform "operations", processor 302 may perform the operations directly and/or facilitate, direct, or cooperate with another device or component to perform the operations.

As illustrated, information handling system 122 employs storage device 314, which may be a hard disk or other types of computer-readable storage devices which may store data that are accessible by a computer, such as magnetic cassettes, flash memory cards, digital versatile disks (DVDs), cartridges, random access memories (RAMs) 310, read only memory (ROM) 308, a cable containing a bit stream and the like, may also be used in the exemplary operating environment. Tangible computer-readable storage media, computer-readable storage devices, or computer-readable memory devices, expressly exclude media such as transitory waves, energy, carrier signals, EM waves, and signals per se.

To enable user interaction with information handling system 122, an input device 322 represents any number of input mechanisms, such as a microphone for speech, a touch-sensitive screen for gesture or graphical input, keyboard, mouse, motion input, speech and so forth. Additionally, input device 322 may receive acoustic or EM measurements from fluid sampling tool 100 (e.g., referring to FIGS. 1 and 2), discussed above. An output device 324 may also be one or more of a number of output mechanisms known to those of skill in the art. In some instances, multimodal systems enable a user to provide multiple types of input to communicate with information handling system 122. Communications interface 326 generally governs and manages the user input and system output. There is no restriction on operating on any particular hardware arrangement and therefore the basic hardware depicted may easily be substituted for improved hardware or firmware arrangements as they are developed.

As illustrated, each individual component described above is depicted and disclosed as individual functional blocks. The functions these blocks represent may be provided through the use of either shared or dedicated hardware, including, but not limited to, hardware capable of executing software and hardware, such as a processor 302, that is purpose-built to operate as an equivalent to software executing on a general-purpose processor. For example, the functions of one or more processors presented in FIG. 5 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 308 for storing software performing the operations described below, and random-access memory (RAM) 310 for storing results. Very large-scale integration (VLSI) hardware embodiments, as well as custom VLSI circuitry in combination with a general-purpose DSP circuit, may also be provided.

Figure 4:
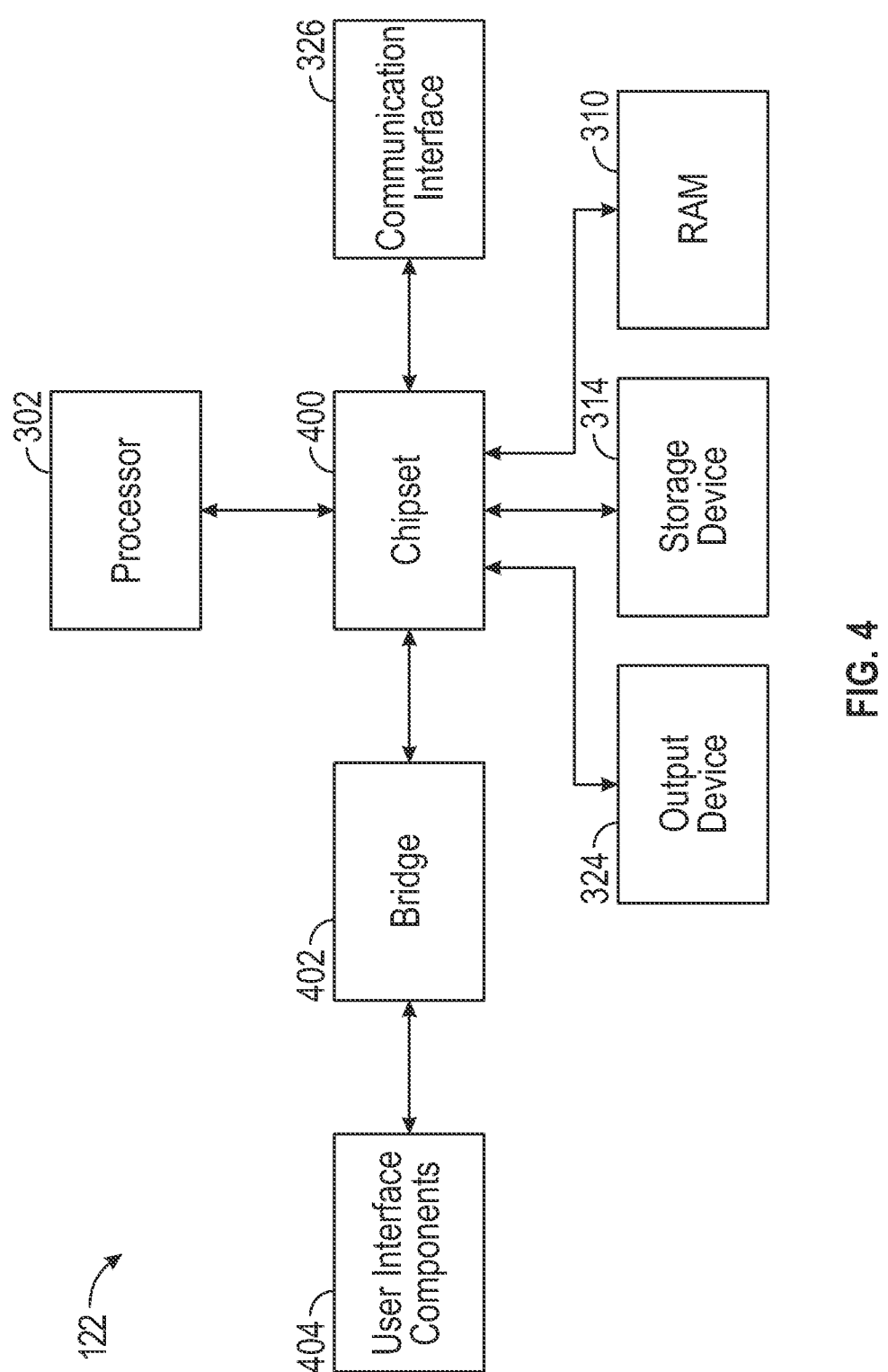
FIG. 4 is a schematic of a chipset that may be utilized by the information handling system.

FIG. 4 illustrates an example information handling system 122 having a chipset architecture for information handling system 122 that may be used in executing the described method and generating and displaying a graphical user interface (GUI). Information handling system 122 is an example of computer hardware, software, and firmware that may be used to implement the disclosed technology. Information handling system 122 may include a processor 302, representative of any number of physically and/or logically distinct resources capable of executing software, firmware, and hardware configured to perform identified computations. Processor 302 may communicate with a chipset 400, discussed below, that may control input to and output from processor 302. In this example, chipset 400 outputs information to output device 324, such as a display, and may read and write information to storage device 314, which may include, for example, magnetic media, and solid-state media. Chipset 400 may also read data from and write data to RAM 310. A bridge 402 for interfacing with a variety of user interface components 404 may be provided for interfacing with chipset 400. Such user interface components 404 may include a keyboard, a microphone, touch detection and processing circuitry, a pointing device, such as a mouse, and so on. In general, inputs to information handling system 122 may come from any of a variety of sources, machine generated and/or human generated.

Chipset 400 may also interface with one or more communication interfaces 326 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 302 analyzing data stored in storage device 314 or RAM 310. Further, information handling system 122 receives inputs from a user via user interface components 404 and execute appropriate functions, such as browsing functions by interpreting these inputs using processor 302.

In examples, information handling system 122 may also include tangible and/or non-transitory computer-readable storage devices for carrying or having computer-executable instructions or data structures stored thereon. Such tangible computer-readable storage devices may be any available device that may be accessed by a general purpose or special purpose computer, including the functional design of any special purpose processor as described above. By way of example, and not limitation, such tangible computer-readable devices may include RAM, ROM, EEPROM, CD-ROM or other optical disk storage, magnetic disk storage or other magnetic storage devices, or any other device which may be used to carry or store program code in the form of computer-executable instructions, data structures, or processor chip design. When information or instructions are provided via a network, or another communications connection (either hardwired, wireless, or combination thereof), to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general-purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing blocks of the methods disclosed herein. The particular sequence of such executable instructions or associated data structures represents examples of corresponding acts for implementing the functions described in such blocks.

In additional examples, methods may be practiced in network computing environments with many types of computer system configurations, including personal computers, hand-held devices, multi-processor systems, microprocessor-based or programmable consumer electronics, network PCs, minicomputers, mainframe computers, and the like. Examples may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Figure 5:
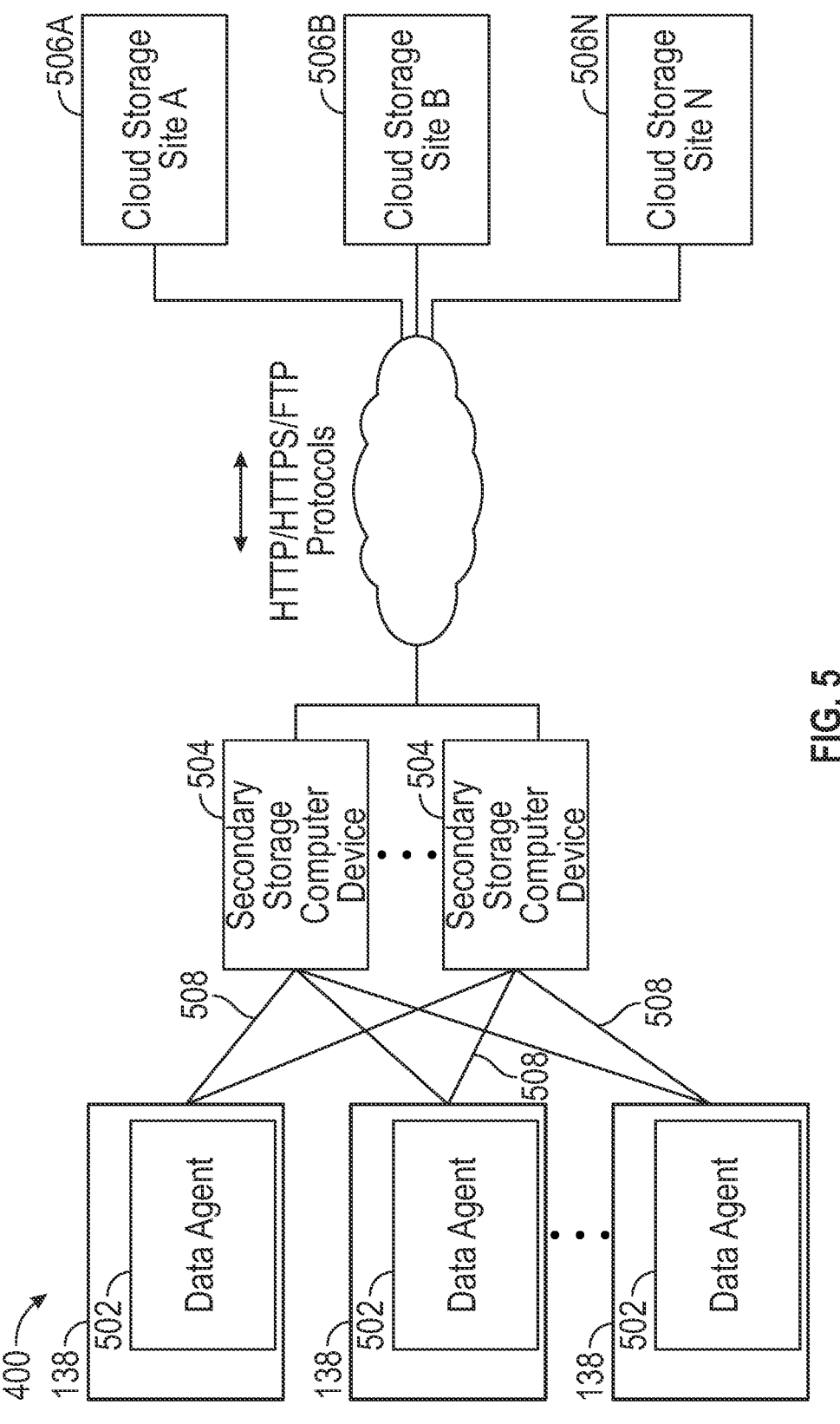
FIG. 5 is a schematic of a schematic for an arrangement of resources on a computer network.

FIG. 5 illustrates an example of one arrangement of resources on a computing network 500 that may employ the processes and techniques described herein, although many others are of course possible. As noted above, an information handling system 122, as part of their function, may utilize data, which includes files, databases, directories, metadata (e.g., access control list (ACLS) creation/edit dates associated with the data, etc.), and other data objects. The data on the information handling system 122 is typically a primary copy (e.g., a production copy). During a copy, backup, archive or other storage operation, information handling system 122 may send a copy of some data objects (or some components thereof) to a secondary storage computing device 504 by utilizing one or more data agents 502.

A data agent 502 may be a desktop application, website application, or any software-based application that is run on information handling system 122. As illustrated, information handling system 122 may be disposed at any rig site (e.g., referring to FIG. 1), off site location, core laboratory, repair and manufacturing center, and/or the like. In examples, data agent 502 may communicate with a secondary storage computing device 504 using communication protocol 508 in a wired or wireless system. Communication protocol 508 may function and operate as an input to a website application. In the website application, field data related to pre- and post-operations, generated DTCs, notes, and/or the like may be uploaded. Additionally, information handling system 122 may utilize communication protocol 508 to access processed measurements, operations with similar DTCs, troubleshooting findings, historical run data, and/or the like. This information is accessed from secondary storage computing device 504 by data agent 502, which is loaded on information handling system 122.

Secondary storage computing device 504 may operate and function to create secondary copies of primary data objects (or some components thereof) in various cloud storage sites 506A-N. Additionally, secondary storage computing device 504 may run determinative algorithms on data uploaded from one or more information handling systems 122, discussed further below. Communications between the secondary storage computing devices 504 and cloud storage sites 506A-N may utilize REST protocols (Representational state transfer interfaces) that satisfy basic C/R/U/D semantics (Create/Read/Update/Delete semantics), or other hypertext transfer protocol ("HTTP")-based or file-transfer protocol ("FTP")-based protocols (e.g., Simple Object Access Protocol).

In conjunction with creating secondary copies in cloud storage sites 506A-N, the secondary storage computing device 504 may also perform local content indexing and/or local object-level, sub-object-level or block-level deduplication when performing storage operations involving various cloud storage sites 506A-N. Cloud storage sites 506A-N may further record and maintain, EM logs, map DTC codes, store repair and maintenance data, store operational data, and/or provide outputs from determinative algorithms that are located in cloud storage sites 506A-N. In a non-limiting example, this type of network may be utilized as a platform to store, backup, analyze, import, preform extract, transform and load ("ETL") processes, mathematically process, apply machine learning models, and augment data sets.

Figure 6:
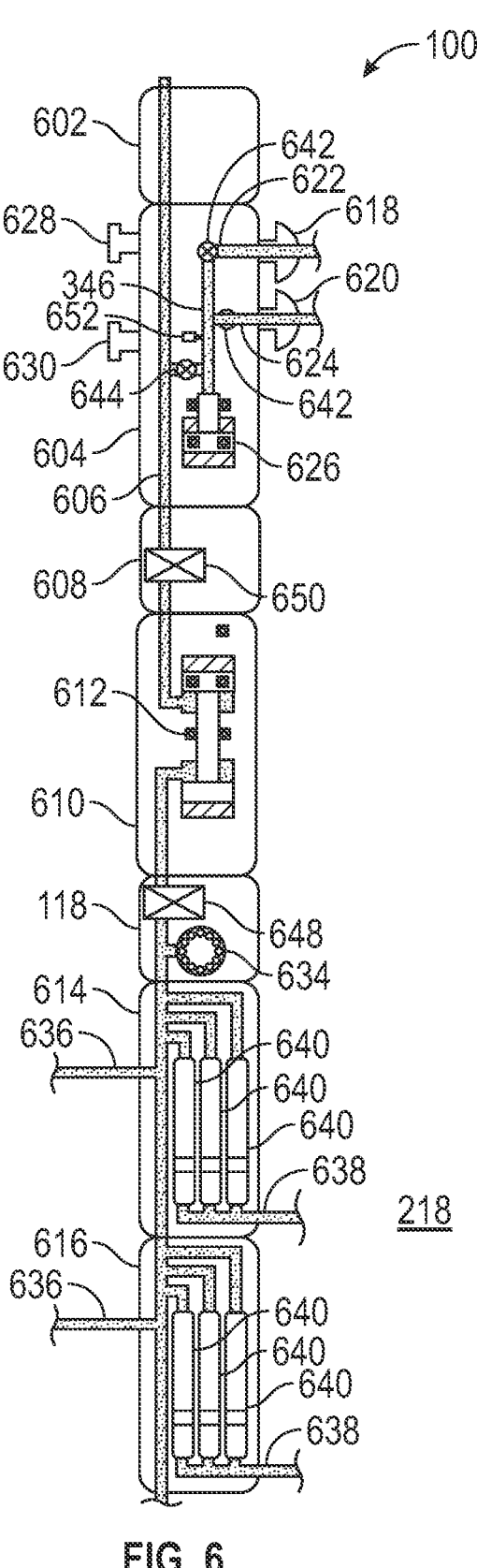
FIG. 6 is a schematic of the fluid sampling tool.

FIG. 6 is a schematic of fluid sampling tool 100. In examples one embodiment, the fluid sampling tool 100 includes a power telemetry section 602 through which the tool communicates with other actuators and sensors 116 in drill string 200 or conveyance 102 (e.g., referring to FIGS. 1 and 2), the drill string's telemetry section 602, and/or directly with a surface telemetry system (not illustrated). In examples, power telemetry section 602 may also be a port through which the various actuators (e.g., valves) and sensors (e.g., temperature and pressure sensors) in the fluid sampling tool 100 may be controlled and monitored. In examples, power telemetry section 602 includes a computer that exercises the control and monitoring function. In one embodiment, the control and monitoring function is performed by a computer in another part of the drill string or wireline tool (not shown) or by information handling system 122 on surface 112 (e.g., referring to FIGS. 1 and 2).

In examples, fluid sampling tool 100 includes a dual probe section 604, which extracts fluid from the reservoir and delivers it to a passageway 606 that extends from one end of fluid sampling tool 100 to the other. Without limitation, dual probe section 604 includes two probes 618, 620 which may extend from fluid sampling tool 100 and press against the inner wall of wellbore 104 (e.g., referring to FIG. 1). Probe channels 622, 624 may connect probes 618, 620 to passageway 606. The high-volume bidirectional pump 612 may be used to pump fluids from the reservoir, through probe channels 622, 624 and to passageway 606. Alternatively, a low volume pump 626 may be used for this purpose. Two standoffs or stabilizers 628, 630 hold fluid sampling tool 100 in place as probes 618, 320 press against the wall of wellbore 104. In examples, probes 618, 620 and stabilizers 628, 630 may be retracted when fluid sampling tool 100 may be in motion and probes 618, 620 and stabilizers 628, 630 may be extended to sample the formation fluids at any suitable location in wellbore 104. Other probe sections include focused sampling probes, oval probes, or packers.

In examples, passageway 606 may be connected to other tools disposed on drill string 200 or conveyance 102 (e.g., referring to FIGS. 1 and 2). In examples, fluid sampling tool 100 may also include a quartz gauge section 608, which may include sensors to allow measurement of properties, such as temperature and pressure, of fluid in passageway 606. Additionally, fluid sampling tool 100 may include a flow-control pump-out section 610, which may include a high-volume bidirectional pump 612 for pumping fluid through passageway 606. In examples, fluid sampling tool 100 may include two multi-chamber sections 614, 616, referred to collectively as multi-chamber sections 614, 616 or individually as first multi-chamber section 614 and second multi-chamber section 616, respectively.

In examples, multi-chamber sections 614, 616 may be separated from flow-control pump-out section 610 by sensor section 632, which may house at least one non-optical fluid sensor 648, 650 and/or at least optical measurement tool 634. It should be noted that non-optical fluid sensor 648, 650 and optical measurement tool 634 may be disposed in any order on passageway 606. Additionally, although depicted in sensor section 632. Both non-optical fluid sensor 648, 650 and optical measurement tool 334 may be disposed along passageway 606 at any suitable location within fluid sampling tool 100.

Non-optical fluid sensor 648, 650 may be displaced within sensor section 632 in-line with passageway 606 to be a "flow through" sensor. In alternate examples, non-optical fluid sensor 648, 650 may be connected to passageway 606 via an offshoot of passageway 606. Without limitation, optical measurement tool 634 may include but not limited to the density sensor, capacitance sensor, resistivity sensor, and/or combinations thereof. In examples, non-optical fluid sensor 648, 650 may operate and/or function to measure fluid properties of drilling fluid filtrate.

Optical measurement tool 634 may be displaced within sensor section 632 in-line with passageway 606 to be a "flow through" sensor. In alternate examples, optical measurement tool 634 may be connected to passageway 606 via an offshoot of passageway 606. Without limitation, optical measurement tool 634 may include optical sensors, acoustic sensors, electromagnetic sensors, conductivity sensors, resistivity sensors, a capacitance sensor, selective electrodes, density sensors, mass sensors, thermal sensors, chromatography sensors, viscosity sensors, bubble point sensors, fluid compressibility sensors, flow rate sensors, microfluidic sensors, selective electrodes such as ion selective electrodes, and/or combinations thereof. In examples, optical measurement tool 634 may operate and/or function to measure drilling fluid filtrate, discussed further below.

Additionally, multi-chamber section 614, 616 may comprise access channel 636 and chamber access channel 638. Without limitation, access channel 636 and chamber access channel 638 may operate and function to either allow a solids-containing fluid (e.g., mud) disposed in wellbore 104 in or provide a path for removing fluid from fluid sampling tool 100 into wellbore 104. As illustrated, multi-chamber section 614, 616 may comprise a plurality of chambers 640. Chambers 640 may be sampling chamber that may be used to sample wellbore fluids, formation fluids, and/or the like during measurement operations.

During downhole measurement operations, a pump out operation may be performed. A pumpout may be an operation where at least a portion of a fluid which may contain solids—(e.g., drilling fluid, mud, filtrate etc.) may move through fluid sampling tool 100 until substantially increasing concentrations of formation fluids enter fluid sampling tool 100. For example, during pumpout operations, probes 618, 620 may be pressed against the inner wall of wellbore 104 (e.g., referring to FIG. 1). Pressure may increase at probes 618, 620 due to compression against the formation 106 (e.g., referring to FIG. 1 or 2) exerting pressure on probes 618, 620. As pressure rises and reaches a predetermined pressure, valve 642 opens so as to close equalizer valve 644, thereby isolating fluid passageway 646 from annulus 218. In this manner, valve 642 ensures that equalizer valve 644 closes only after probes 618, 620 has entered contact with mud cake (not illustrated) that is disposed against the inner wall of wellbore 104. In examples, as probes 618, 620 are pressed against the inner wall of wellbore 104, the pressure rises and closes the equalizer valve in fluid passageway 646, thereby isolating the fluid passageway 646 from the annulus 218. In this manner, the equalizer valve in fluid passageway 646 may close before probes 618, 620 may have entered contact with the mud cake that lines the inner wall of wellbore 104. Fluid passageway 646, now closed to annulus 218, is in fluid communication with low volume pump 626.

As low volume pump 626 is actuated, formation fluid may thus be drawn through probe channels 622, 624 and probes 618, 620. The movement of low volume pump 626 lowers the pressure in fluid passageway 646 to a pressure below the formation pressure, such that formation fluid is drawn through probe channels 622, 624 and probes 618, 620 and into fluid passageway 646. Probes 618, 620 serves as a seal to prevent annular fluids from entering fluid passageway 646. Such an operation as described may take place before, after, during or as part of a sampling operation.

With low volume pump 626 in its fully retracted position and formation fluid drawn into fluid passageway 646, the pressure will stabilize and enable pressure sensor 652 to sense and measure formation fluid pressure. The measured pressure is transmitted to information handling system 122 disposed on formation testing tool 100 and/or it may be transmitted to the surface via mud pulse telemetry or by any other conventional telemetry means to an information handling system 122 disposed on surface 112.

During this interval, pressure sensor 652 may continuously monitor the pressure in fluid passageway 646 until the pressure stabilizes, or after a predetermined time interval. When the measured pressure stabilizes, or after a predetermined time interval, for example at 1800 psi, and is sensed by pressure sensor 652 the drawdown operation may be complete.

Next, high-volume bidirectional pump 612 activates and equalizer valve 644 is opened. This allows for formation fluid to move toward high-volume bidirectional pump 612 through passageway 606. Formation fluid moves through passageway 606 to sensor section 632. Once the drilling fluid filtrate has moved into sensor section 632 high-volume bidirectional pump 612 may stop. This may allow the drilling fluid filtrate to be measured by optical measurement tool 634 within sensor section 632. Without limitation, any suitable properties of the formation fluid may be measured utilizing an optical measurement tool.

Figure 7:
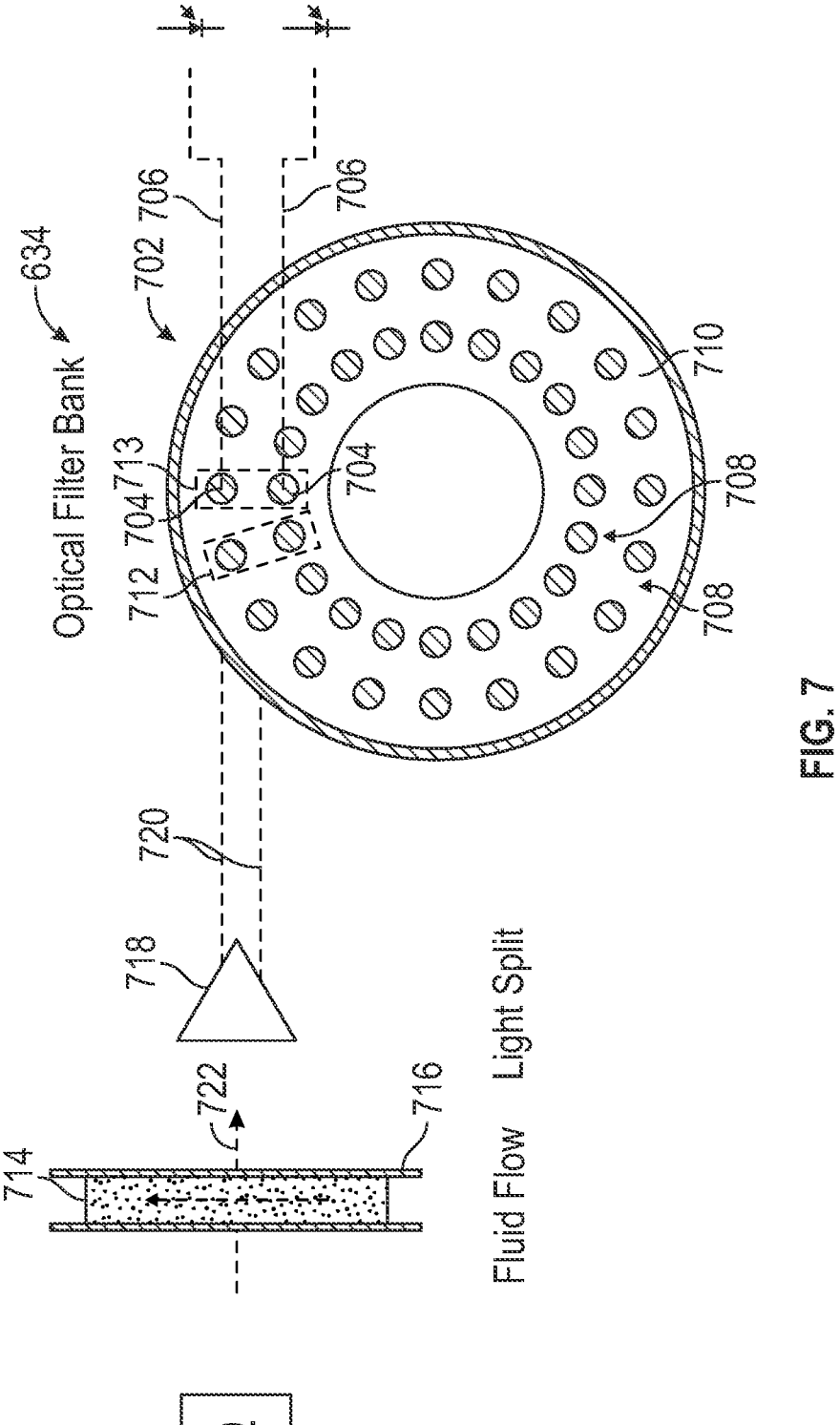
FIG. 7 depicts a hardware configuration of a dynamic subsurface optical measurement tool.

FIG. 7 depicts a hardware configuration of a dynamic subsurface optical measurement tool 334. It should be noted that a channel disclosed herein, may be a measurement of the light transmittance through an optical filter. Optical measurement tool 634 may include a light source 700, a filter bank 702 comprising a plurality of optical filters 704

(measurement of the light transmittance through an optical filter 704 is called a channel 706) configured as two rings 708 on optical plate 710, within a channel pair 712 on each azimuth. It should be noted that each channel 706 may be designed, based on the construction of each channel 706 respective optical filter 704, to measure different properties of fluid sample 714. During the rotation of optical plate 710, the two optical filters 704 on a channel pair 712 may be synchronized spatially or in time to measure substantially the same fluid sample 714 in viewing area 716. As discussed below, and illustrated in FIG. 7, an active channel pair 713 is a channel pair 712 in which optical measurements are being taken to form one or more channels 706. In some embodiments, channel pairs 712 may be near synchronized such that channel pairs 712 have a sufficient probability of observing the same phase, i.e., better than 10% but more desirably more than 50% and yet more desirably more than 80%. In other embodiments, more than two channels 706 may be sufficiently synchronized according to a desired probability of observing a single phase in time or space. A velocity calculation of the fluid phase specific velocities may be used to aid synchronization over longer distances, or time. Alternatively, distribution calculations, or autocorrelation calculations may be used to improve synchronization over longer distances or time. If the channels are sufficiently close in distance or time, the channel signals may not need additional efforts of synchronization. During measurement operations, fluid samples 714 (which is formation fluid from passageway 606) may flow through viewing area 716 as a non-limiting example constructed by a set of windows or other transparent region of the flow path. Alternatively, the viewing region or viewing area might not be transparent to visible light but rather to the form of energy used to measure the fluid characteristics for a given sensor. As such a viewing region or area for an acoustic sensor would ideally have a low acoustic impedance even if it is not transparent to visible light. Alternatively, the viewing region or area may be transparent (i.e., pass energy with low attenuation) to infrared light, or magnetic fields instead of visible light. In some embodiments for some sensors, viewing area 716 or area is more generally a measurement region or area as is the case with some phase behavior sensors or some density sensors. In examples, viewing area 716 may be at least a part of passageway 606 and/or a branch off of passageway 606). In one nonlimiting embodiment, light 722 absorbed by fluid sample 714 may be split into at least two ray paths 720, through a prism 718. Split light rays 720 may be measured by detectors, not shown, as they pass through channel pair 712 separately. Filter bank 702 may rotate to another channel pair 712 after the measurement of each channel 706 from channel pair 712 and may dynamically gather an optical spectra measurement of all channels after a full sampling channel rotation. It should be noted, the methods disclosed herein may not be limited in simultaneous measurements of a channel pair 712 (two optical filters 704 and their respective channel 706) but may also apply to cases with one or more optical filters 704 or filter banks 702, at least one channel 706, or, alternatively, two or more channels 706.

As described, optical measurement tool 634 may be used in a downhole environment to perform measurements on fluid samples 714. Analysis of collected data may occur at various locations in a system or at various steps in a method in accordance with the present disclosure. For example, processing of the collected data may occur at any suitable location including, without limitation, at fluid analysis module 118 and/or information handling system 122.

FIG. 8 illustrates a workflow 800 to determine a concentration of ions. For this disclosure, workflow 800 may be processed and/or performed on information handling system 122. It should be noted, for this disclosure, ions that may be identified comprise Sodium, Potassium, Calcium, Magnesium, Manganese, Strontium, Barium, Iron(II), Iron(III), Chromium(II), Chromium(III), Copper(I), Copper(II), Fluoride, Bromide, Iodide, Carbonate, Oxalate, Nitrite, Nitrate, Phosphite, Phosphate, Sulfite, Sulfate, Hydrogen Carbonate, Hydrogen Sulfite ("Bisulfite"), Hydrogen Sulfate ("Bisulfate"), Hydronium, Hydrogen Phosphate, Dihydrogen Phosphate, Chromate, Dichromate, Acetate, Thiosulfate, Hydride, Lithium, Zinc, Ammonium, Cyanide, Permanganate, Mercury (I), Mercury (II), and any combinations thereof. As illustrated, workflow 800 may begin in block 802. In block 802, fluid sampling tool 100 may be deployed downhole. As described previously, dual probe section 604 of fluid sampling tool 100 may be pressed against the inner wall of wellbore 104. Workflow 800 may proceed to block 804, where a pumpout operation may occur. In block 804, fluid sampling tool 100 may be used to pump out water fluid from the formation and analyze with optical spectroscopy, such as via optical measurement tool 634 and fluid analysis module 118. In block 806, fluid analysis module 118 and/or information handling system 122 may be used to interpret the information gathered by the optical measurement tool 634 and identify a water peak spectrum in the near infrared region (1420 nm). In block 808, fluid analysis module 118 or information handling system 122 may fit Gaussian and Lorentzian curves to identify a cumulative fit that overlays the water peak spectrum. In block 810, fluid analysis module 118 or information handling system 122 may analyze the properties of the Gaussian and Lorentzian curves that correspond to Peak Height, FWHM, and Area, and rationalize with temperature and known ion concentration levels. In block 812, fluid analysis module 118 or information handling system 122 may form a regression model that may be linear, Principal Component Regression (PCR), or Partial Least Squares (PLS) that fits the parameters and forms an appropriate model to different levels of concentration of ions.

The model formed in block 812 during workflow 800 may be used to carry out a variety of executable instructions including, among others, distinguishing filtrate from water. In addition, the model may be used to show unique characteristics between waters in-situ. As discussed, the model may take as inputs one or more parameters, or yield as outputs one or more parameters. Parameters may include ion concentration, temperature, salinity, known or estimated water chemistry, relative amounts of one or more types of fluid or component present in a fluid sample, etc.

As discussed previously, it may be challenging using conventional methods to distinguish formation water from a water-based mud filtrate. This is further compounded when distinguishing between injected and formation waters under in-situ temperature and pressure conditions. The prevailing industry method is to analyze fluids on surface at a laboratory. However, this incurs both time and potential representation inaccuracies. It is therefore prudent to expand the boundary of Downhole Fluid Analysis (DFA) into water chemistry applications to recognize ionic properties within fluids. Certain embodiments of the present disclosure may be well suited to equip a Wireline Formation Tester (WFT) with DFA based Optical Spectroscopy to quantify ion concentration and thus reservoirs connectivity.

Two applications of using downhole ion data are highlighted in a wireline acquisition program. In the first case, downhole ion values are used to "fingerprint" fluids to differentiate between injected or disposal water, and formation water. A second case is presented to show how a petrophysical interpretation is optimized through using multiple ion values instead of a single assumption.

A set of experiments were designed as a proof-of-concept experiment and validation testing. A matrix of ten saline water samples were formulated for proof-of-concept laboratory experiments, as well as optical sensor validation testing. Five ionic component concentrations ($K^+$, $Mg_2^+$, $Ca_2^+$, $Cl-$, and $Na^+$) were systematically varied to represent a range of typical formation water saline chemistries. Sulfonates and bicarbonates were not included at this time. The properties of all ten samples are listed in Table 1 below:

TABLE 1

| | | | Experimental design of samples used for proof-of-concept experiment and validation testing. | | | | |
|---|---|---|---|---|---|---|---|
| Sample # | K wt % | Mg wt % | Ca wt % | Cl wt % | Na wt % | TDS mg/L | Density mg/L |
| 0 | 0.00% | 0.00% | 0.00% | 0.00% | 0.00% | 0 | 1 |
| 1 | 0.01% | 0.01% | 0.06% | 0.87% | 0.48% | 14435 | 1.009 |
| 2 | 0.02% | 0.01% | 0.18% | 1.99% | 1.05% | 33294 | 1.021 |
| 3 | 0.05% | 0.02% | 0.29% | 3.84% | 2.09% | 65507 | 1.042 |
| 4 | 0.05% | 0.02% | 0.28% | 5.64% | 3.27% | 98476 | 1.064 |
| 5 | 0.08% | 0.02% | 0.32% | 7.79% | 4.59% | 139639 | 1.091 |
| 6 | 0.19% | 0.05% | 0.77% | 8.51% | 4.44% | 153478 | 1.1 |
| 7 | 0.31% | 0.08% | 1.01% | 9.41% | 4.62% | 171382 | 1.111 |
| 8 | 0.10% | 0.06% | 0.28% | 12.18% | 7.42% | 230240 | 1.149 |
| 9 | 0.18% | 0.14% | 0.89% | 13.02% | 7.06% | 246946 | 1.16 |

Figure 9:
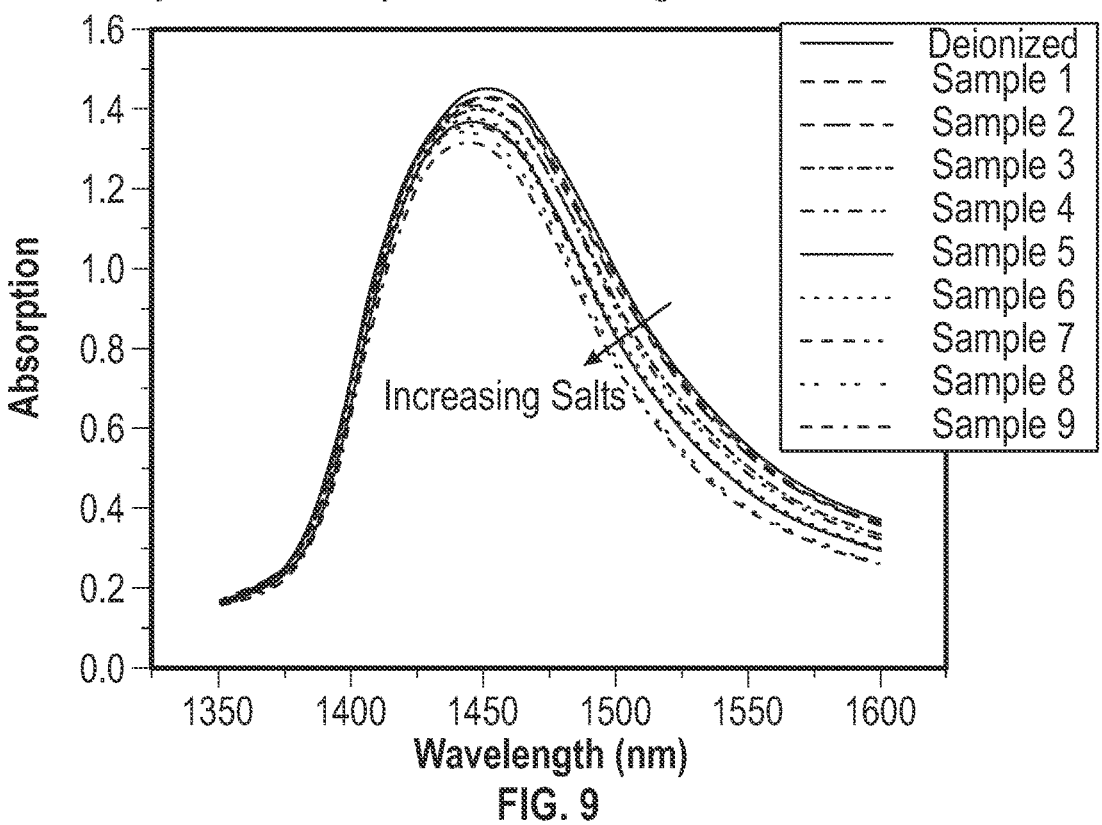
FIG. 9 is a graph illustrating laboratory spectra, centered on the water absorbance peak near ~1450 nm, for ten samples.
Figure 10:
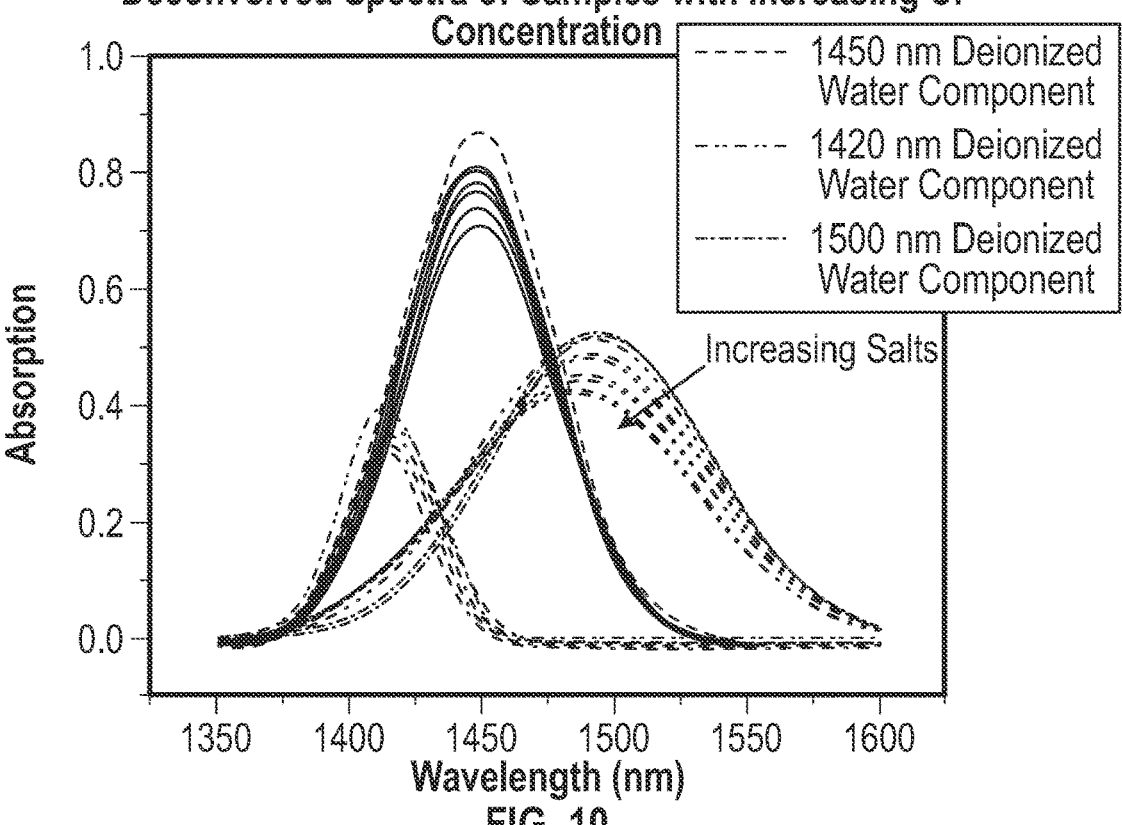
FIG. 10 is a graph illustrating a deconvolved optical spectrum of water for each one of the ten samples.

Each sample was measured on a laboratory grade UV-NIR spectrometer (PerkinElmer Lambda1050) at room temperature and pressure conditions. The laboratory spectra, centered on the water absorbance peak near ~1450 nm, for all ten samples is plotted in FIG. 9. Without any peak fitting or spectral decomposition, a clear trend is observed with the peak broadening (full width half maximum, FWHM) and center peak position decreasing with increasing chloride/salt concentration. Sensitivity to less than 1% change in sodium and chloride content is visibly discernable from the laboratory spectra. A three component Gaussian fit was performed to isolate the ionic contributions more accurately and quantify the perturbations due to the chloride ions on the water absorbance peak for each spectrum. The results for the Gaussian decomposition fits are illustrated in FIG. 10. The three component Gaussian fit for one spectrum is illustrated in FIG. 11.

Figures 11, 12:
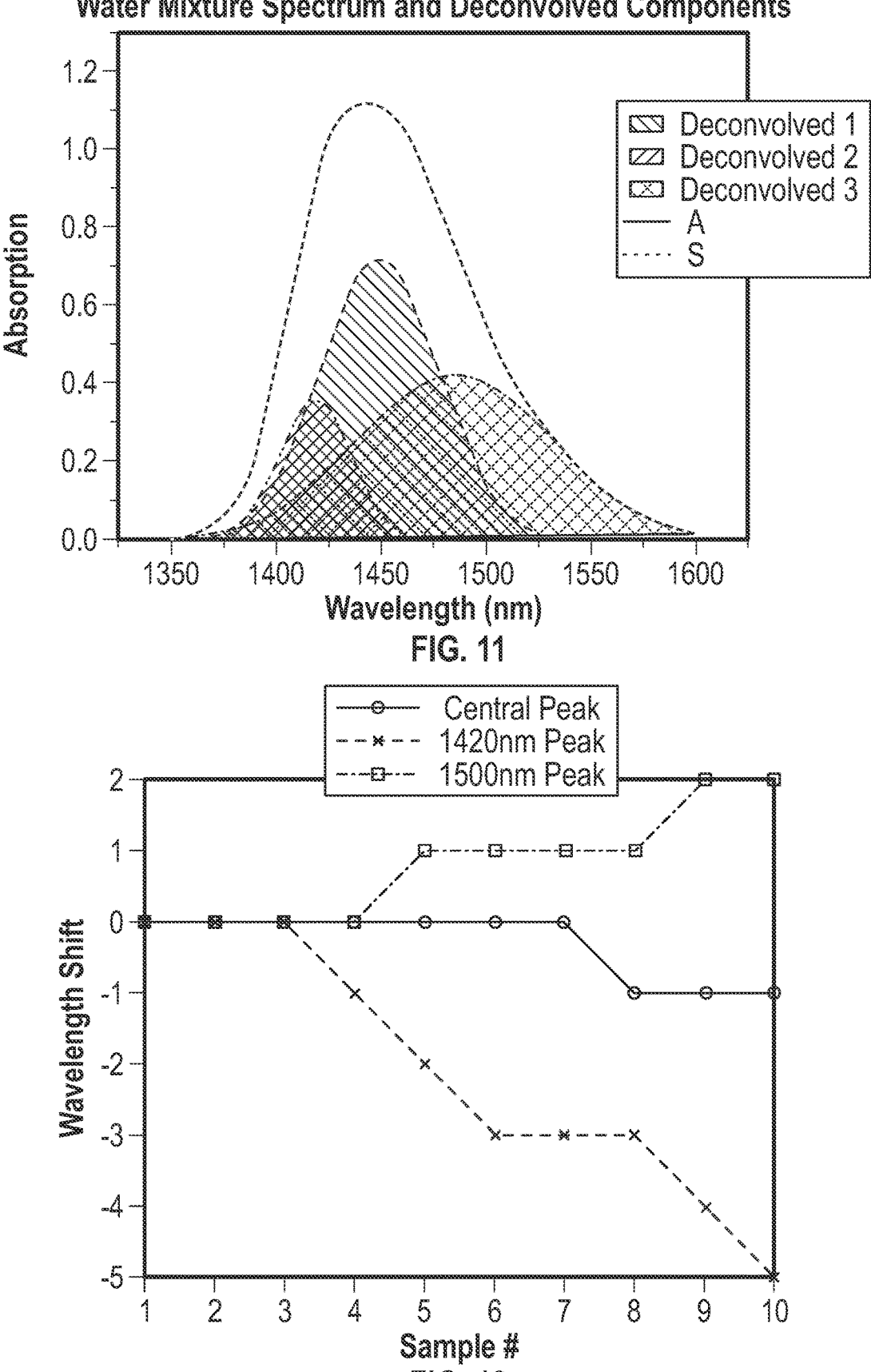
FIG. 11 is the deconvolved spectrum of water using the three component Gaussian fit.
FIG. 12 illustrates the Gaussian peak shift for each chloride sample.

FIG. 12 illustrates the Gaussian peak shift for each chloride sample. First, only the far left peak (black, centered at ~1420 nm) exhibits a strong dependence of peak shifting with increasing chloride concentration. The other two peaks, located at ~1450 nm (red) and ~1500 nm (blue) show a much weaker shift in wavelength with chloride concentration, but correlate to cations within the solution. The quantitative results of peak shifting with chloride concentration are plotted in FIG. 12. No discernable shift in spectrum is observed for any sample with less than ~2 wt % chloride concentration. Also, the 1420 nm peak (exhibiting the largest dependence on peak shifting) has a plateau for the $6^{th}$-$8^{th}$ samples corresponding to those samples with similar sodium concentration. Since the chloride, total salt content, and densities for all samples are linearly increasing, this trend suggests that the wavelength shift for the 1420 nm peak is primarily correlated to the sodium concentration.

Figure 13:
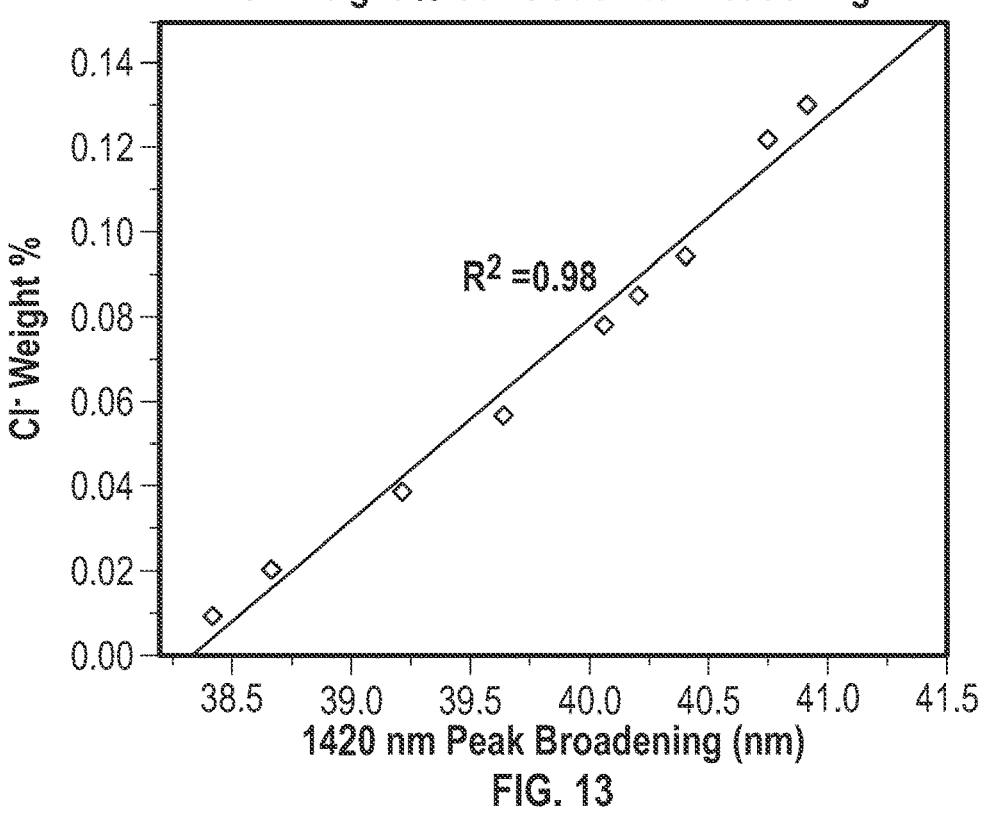
FIG. 13 illustrates the dependence of the Gaussian water peak broadening upon chloride concentration.

FIG. 13 illustrates the dependence of the Gaussian water peak broadening upon chloride concentration. The ~1420 nm peak's broadening exhibits a strong linear dependence on chloride concentration, which is not observed for the other 2 peaks. The results in FIG. 13 demonstrate a ~7% dynamic change in peak FWHM for the entire range of chlorides in the sample set.

Figure 14:
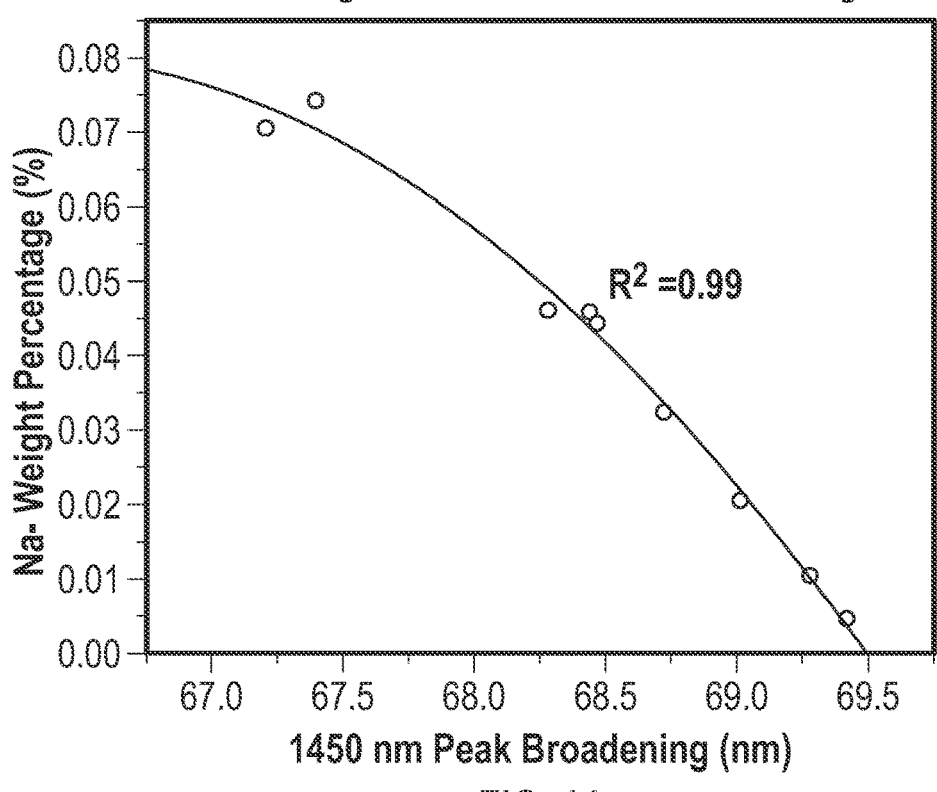
FIG. 14 illustrates the Gaussian peak broadening at 1450 nm center correlation with sodium concentration.
Figure 15:
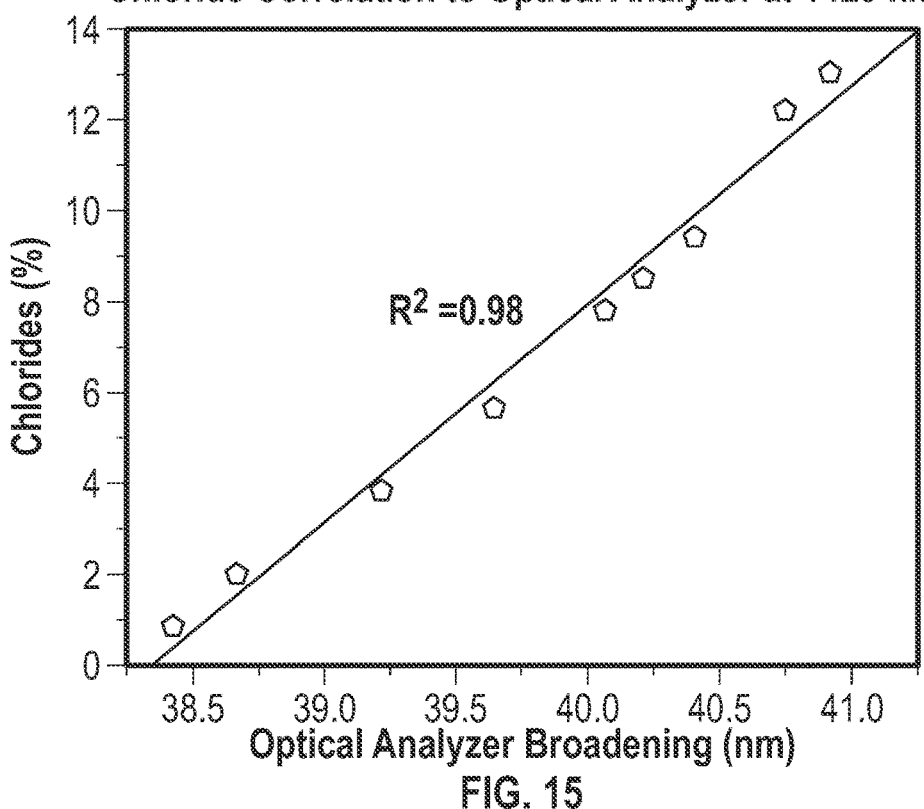
FIG. 15 shows the linear correlation between the optical analyzer Gaussian peak broadening at 1420 nm and chloride concentration.

FIG. 14 illustrates the Gaussian peak broadening at 1450 nm center correlation with sodium concentration. An inverse correlation is also observed for the central peak's (~1450 nm) broadening with sodium concentration. Further, samples #6-8 have a plateau in their FWHM that is consistent with the sodium concentration trend, similar to the peak shifting observed at ~1420 nm peak. Finally, although the right peak (at ~1500 nm in FIG. 10) has a strong amplitude reduction, there is very negligible dependence on peak shifting and/or broadening for all the samples measured. These results demonstrate that different saline water absorbance spectra may be successfully decomposed into a linear combination of Gaussian peaks. Further, the center wavelength and broadening (FWHM) of the Gaussian peaks trend linearly with chloride and sodium concentrations and suggest a linear or multivariate model may be developed to predict the chloride concentration for an unknown sample. The same ten samples from Table 1 used for the proof-of-concept experiments in the laboratory were also measured with the downhole optical sensor. FIG. 15 shows a strong linear correlation between the optical analyzer Gaussian peak broadening at 1420 nm and chloride concentration. The optical analyzer measurement at 1420 nm can be used to calculate the ion concentrations very well.

Figure 16:
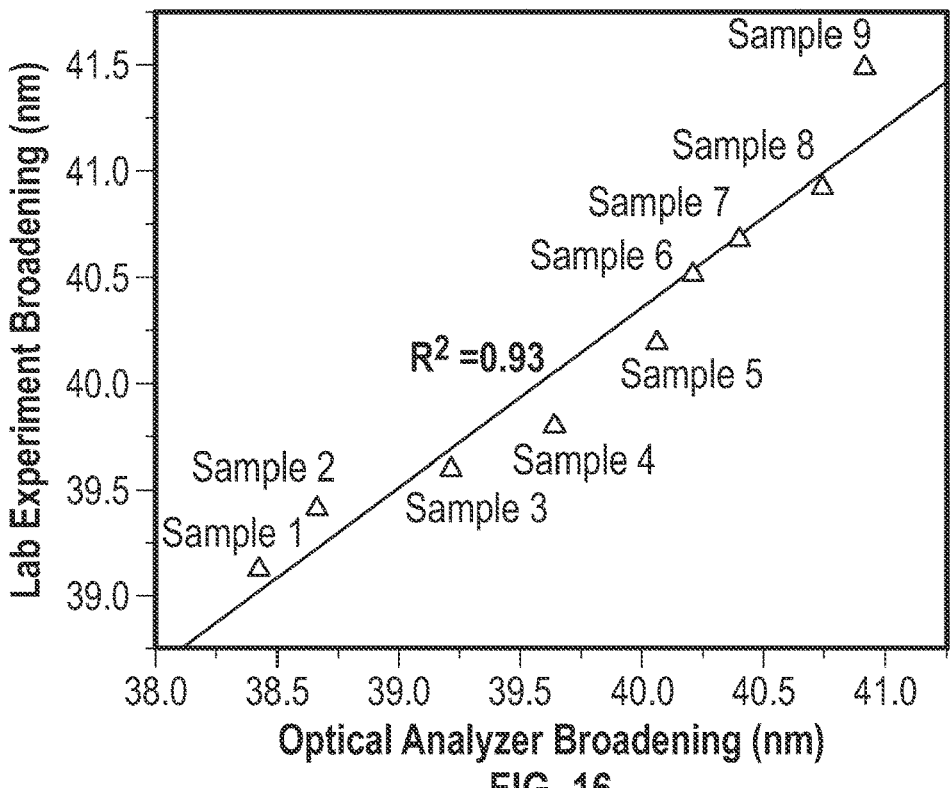
FIG. 16 shows the correlation between the chloride concentration obtained from laboratory measurement and those obtained with the optical analyzer.

FIG. 16 shows a strong correlation between the chloride concentration obtained from laboratory measurement and those obtained with the optical analyzer. The correlation coefficient lends credibility that the optical sensor may successfully deconvolve the water peak and correlate to ion components.

With the deconvolved water spectrum of FIG. 11, there exist a set of unique spectral attributes that describe the absorbance, namely:

$$\alpha_{1420}, \sigma_{1420}, \lambda_{0_{1420}}, \alpha_{1450}, \sigma_{1450}, \lambda_{0_{1450}}, \alpha_{1500}, \sigma_{1500}, \lambda_{0_{1500}}$$

Using these attributes, a linear system of equations may be created to represent each ion concentration to the spectral attributes:

$$\text{Concentration} = x_1\alpha_{1420} + x_2\sigma_{1420} + x_3\lambda_{0_{1420}} + x_4\alpha_{1450} + x_5\sigma_{1450} + x_6\lambda_{0_{1450}} \qquad \text{Equation 6}$$

where $[x_1 \ldots x_n]$ is a set of coefficients used to resolve concentration and n is the number of samples.

Ionic concentrations may be measured at ambient conditions in a laboratory environment. This resulting solution is represented below:

$$[Y]=[A]x \qquad \text{Equation 7}$$

where [Y] is the ion concentration array, [A] is the Spectral Attributes array for samples measured at ambient conditions, and x is the coefficients used to constrain the solution. The arrays are represented as:

$$[Y] = \begin{bmatrix} \text{Sample 1} \\ \vdots \\ \text{Sample } n \end{bmatrix} \qquad \text{Equation 8}$$

$$[A] = \begin{bmatrix} \alpha_{1420} & \cdots & \lambda_{0_{1500}} \\ \vdots & \ddots & \vdots \\ \alpha_{1420} & \cdots & \lambda_{0_{1500}} \end{bmatrix} \qquad \text{Equation 9}$$

-continued $$x = \begin{bmatrix} x_1 \\ \vdots \\ x_n \end{bmatrix} \qquad \text{Equation 10}$$

This same model was represented for both an anion (chlorides) and different cations (sodium, magnesium, and calcium) that represent the solution in the samples. A NIR spectroscopy response to a fluid is sensitive to pressure and temperature variation. In order to represent the concentrations in situ, the Proof of Concept samples were subjected to measurements at various temperatures and pressure above ambient. Specifically, coefficients are a solution to the following equations:

$$[Y]=[A]_p x_p \qquad \text{Equation 11}$$

$$[Y]=[A]_t x_t \qquad \text{Equation 12}$$

where $x_p$ and $x_t$ are coefficients that constrain the ionic concentration to a specific pressure (p) and temperature (t).

The Spectral Attributes array at temperature and pressure $([A]_p, [A]_t)$ have all the elements described as a function of the respective pressure or temperature. For each of the three center frequencies, the spectral attributes are:

$$(\alpha,\sigma,\lambda_0)_{pressure\ compensated}=f(p) \qquad \text{Equation 13}$$

$$(\alpha,\sigma,\lambda_0)_{temperature\ compensated}=f(t) \qquad \text{Equation 14}$$

With the pressure and temperature coefficients, the resulting coefficient array to resolve concentration to the original Equation 11 is obtained through multiple linear regressions: x is linearly regressed from $x_p$ to $x_t$.

Figure 17:
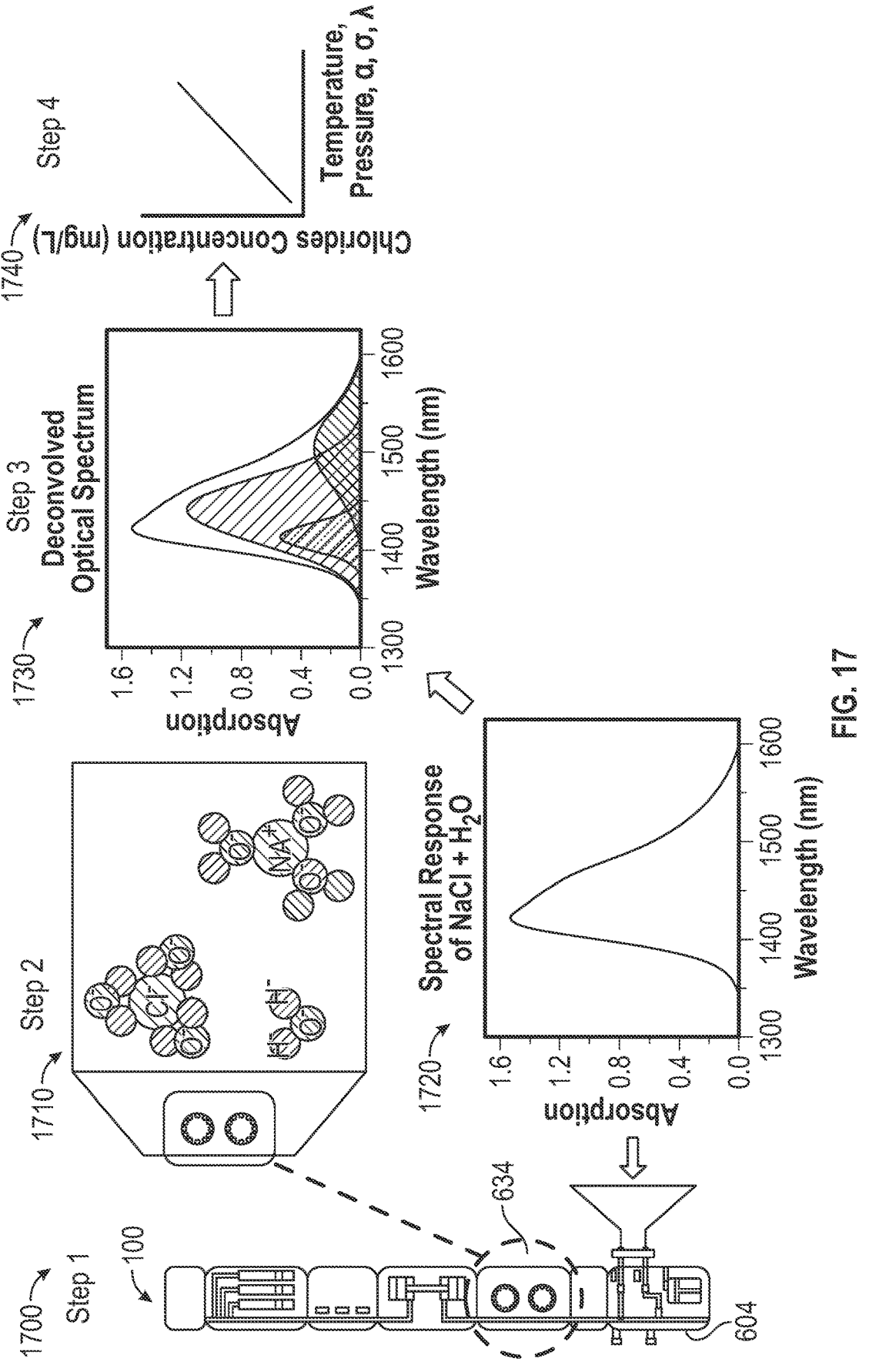
FIG. 17 shows the primary steps for a wireline formation tester to acquire and model concentrations of anions and cations in a water mixture.

FIG. 17 shows the primary steps for fluid sampling tool 100 (e.g., referring to FIG. 1) to acquire and model concentrations of anions and cations in a water mixture. A measurement operation 1700 comprises four steps when fluid sampling tool 100 is placed in a water bearing zone and data is recorded in situ at downhole pressure and temperature. Step 1 includes fluid sampling tool 100 pumping fluid through its passageway for fluid sampling tool 100 clean up from mud filtrate which penetrated inside the formation, and steps 2-4 include the processing of the downhole sensor signal acquired within the fluid sampling tool. Specifically, in step 1, fluid sampling tool 100 such as a fluid analysis and sampling tool or a formation tester fluidly connects to a formation in the wellbore through the at least one probe of the dual probe section 604 (referring to FIG. 6) and starts drawing the formation fluid through at least one passageway that passes through the at least one probe of the dual probe section 604 and the downhole spectroscopy device 634. In step 2, as fluid sampling tool 100 begins pumping out fluid, downhole spectroscopy measurement device 634 records properties of the fluid 1710 as the fluid being pumped is first contaminated by mud filtrate which infiltrated the formation during and after drilling. Downhole spectroscopy measurement device 634 may include multiple broad bandpass filters based on compressive sensing principle, wherein the compressive sensing principle comprises a compressive sensing reconstruction algorithm and a fluid spectral database. As pumping continues and the volume of fluid being extracted from the formation grows, mud filtrate contamination decreases until the fluid being pumped is identical to formation water. The recorded properties are then transferred to information handing system 122 (e.g., referring to FIG. 1) for analyses of the spectrum response to sodium chloride in water 1720, for instance. Analysis of spectrum 1720 includes spectral deconvolution to quantify ions concentrations, wherein the spectral deconvolution comprises Gaussian, Lorentzian or Voight Curve with Gaussian and Lorentzian addition. For instance, peak height, or Full Width Half Max (FWHM), or integrated area, or a combination thereof of at least one of the Gaussian and Lorentzian curves in combination with temperature and a model can be used to quantify ion concentrations.

In the case where Water-Based Mud (WBM) is used, this filtrate may have a predetermined chloride concentration in accordance with the mud recipe, and an associated signature in the Near Infrared (NIR) spectrum. In Step 3, using information handing system 122, spectral response of sodium chloride in water 1720 is deconvolved into separate Gaussian contributions at the 1420 nm, 1450 nm, and 1500 nm peak frequencies as illustrated in its deconvolved optical spectrum 1730. As the contamination of the sample fluid starts to reduce, the fingerprint of the three peaks will vary, representing a change in the chloride structure. In Step 4, the characteristics of each deconvolved peak may be used by information handling system 122 in the Principal Component Analysis Regression Algorithm of the present disclosure to generate a concentration component as illustrated in the graph of the chloride concentration as a function of temperature, pressure, and time in 1740, for instance.

Interpretation of measurement data may assume a single ion concentration in a sample or multiple. In embodiments where multiple ion concentrations are assumed, such as for samples comprising a plurality of water types or a mixture of fluids from a plurality of water sources, accuracy of a model may be optimized. Accordingly, a model based on an assumption of multiple ion concentrations may be better suited to recognize and identify each of a diversity of components in a sample than conventional means.

To date, the industry has been unable to quantify ions as a contribution to Water Chemistry in situ. Certain embodiments of the present disclosure are well adapted to Wireline pump-out and sampling to distinguish ions as well as to using Spectral Deconvolution techniques within a DFA. Such methods have broad applications including, among others, to diagnose water production and to assess compatibility for Salt Water Disposal (SWD) and Carbon Capture and Sequestration (CCS) projects.

As discussed, methods and systems in accordance with the present disclosure may be equipped to carry out Spectral Deconvolution in addition to downhole fluid analysis. Spectral Deconvolution may be used to sparse out a singular optical spectrum into a plurality of deconvolved components.

Models in accordance with the present disclosure may be developed experimentally to determine ion concentrations at varying fluid salinities. These models may include, among other parameters, temperature and/or spectral components. These experimentally derived models may distinguish a mud filtrate from water as well as between waters in-situ. Fluid analysis module 118 may incorporate the Spectral Deconvolution techniques shown and described for FIG. 10 and throughout the present disclosure. For example, light absorption responses measured by optical measurement tool 634 may be interpreted by fluid analysis module 118 according to the techniques described for FIG. 10 to yield deconvolved spectra which may be used to differentiate between water sources, to determine ionic properties of fluid samples, and/or to quantify ion concentrations.

This disclosure is the first of any similar industry technology to disclose the use of Spectral Deconvolution as a means to resolve characteristics of the fluid. Current technologies merely utilize the peak height of the original spectrum that a Downhole Fluid Analyzer measures. While possessing at least some degree of accuracy, such conventional methods merely relying on peak height are limited to generally representing fluid properties of samples. Furthermore, conventional methods generally fail to provide water chemistry information and ion concentration information. In contrast, certain embodiments in accordance with the present disclosure are equipped with means to provide specific information regarding fluid composition and associated fluid properties of individual and mixed components. Using this method, this is the first attempt in the industry to provide a component corresponding to water chemistry (ions), which to date is only provided by the lab. There are several other deliverables of water chemistry that a lab provides and can be investigated from this study. Ions may be a discriminator to distinguish water-based mud filtrate and formation water. In addition, if there are multiple water samples taken in a well, ions may be used to "fingerprint" them and show which are dissimilar.

As shown and discussed, the present disclosure provides systems and methods having improved abilities to 1) reduce delay in fluid sampling of reservoirs, 2) improve representational accuracy of samples, 3) perform sampling and analysis in-situ, 3) more reliably quantify ions, and 4) differentiate between each of a plurality of components from various water sources present in a downhole environment. The systems and methods for determining ion concentration in a sample may include any of the various features of the systems and methods disclosed herein, including one or more of the following statements.

Statement 1: A method may comprise disposing a fluid sampling tool into a wellbore. The fluid sampling tool may comprise at least one probe to fluidly connect the fluid sampling tool to a formation in the wellbore and at least one passageway that passes through the at least one probe and into the fluid sampling tool. The method may further comprise drawing a formation fluid from a first sampling zone, as a fluid sample, through the at least one probe and through the at least one passageway and analyzing the fluid sample in the fluid sampling tool for one or more ion components.

Statement 2: The method of statement 1, wherein analyzing the fluid sample comprises using a downhole spectroscopy device and spectral deconvolution to quantify ions concentrations.

Statement 3: The method of statement 2, wherein the spectral deconvolution comprises Gaussian, Lorentzian or Voight Curve with Gaussian and Lorentzian addition.

Statement 4: The method of statement 3, wherein peak height, or Full Width Half Max (FWHM), or integrated area, or a combination thereof of at least one of the Gaussian and Lorentzian curves in combination with temperature and a model are used to quantify ion concentrations.

Statement 5: The method of statements 1 or 2, wherein analyzing the fluid sample comprises using a downhole optical sensor comprising multiple broad bandpass filters based on compressive sensing principle.

Statement 6: The method of statement 5, wherein the compressive sensing principle comprises a compressive sensing reconstruction algorithm and a fluid spectral database.

Statement 7: The method of any previous statements 1, 2, or 6, wherein the ion components are chloride ions.

Statement 8: The method of any previous statements 1, 2, 6, or 7, wherein the ion components are either calcium ions, potassium ions, magnesium ions, or sulfate ions.

Statement 9: The method of any previous statements 1, 2, or 6-8, wherein the ion components are hydronium ions.

Statement 10: The method of any previous statements 1, 2, or 6-9, wherein the ion components are sodium ions.

Statement 11: The method of any previous statements 1, 2, or 6-10, wherein the ion components are lithium ions.

Statement 12: The method of any previous statements 1, 2, or 6-11, wherein the ion components are iron ions.

Statement 13: The method of any previous statements 1, 2, or 6-12, wherein the ion components are carbonate ions.

Statement 14: The method of any previous statements 1, 2, or 6-13, wherein the ion components are mercury ions.

Statement 15: The method of any previous statements 1, 2, or 6-14, further distinguishing fluid sample passing through the at least one passageway being contaminated by water-based mud filtrate through ions quantification.

Statement 16: The method of any previous statements 1, 2, or 6-15, further drawing a formation fluid from a second or more sampling zone and determining whether fluid sample in the at least one passageway being from the same formation fluid as the first sampling zone through ions quantification.

Statement 17: A method of quantifying ions may comprise using an optical sensor comprising multiple broad bandpass filters, using a compressive sensing reconstruction algorithm comprising first two principal components, using a fluid spectral database, using a clustering method for fluid identification, and using spectral deconvolution to quantify ions concentrations.

Statement 18: The method of statement 17, wherein the spectral deconvolution comprises Gaussian, Lorentzian or Voight Curve with Gaussian and Lorentzian addition.

Statement 19: The method of statement 18, wherein peak height, or Full Width Half Max (FWHM), or integrated area, or a combination thereof of at least one of the Gaussian and Lorentzian curves in combination with temperature and a model are used to quantify ion concentrations.

Statement 20: The method of statements 17 or 18, wherein quantifying ions comprises quantifying ions contribution to water chemistry in-situ.

The preceding description provides various examples of the systems and methods of use disclosed herein which may contain different method steps and alternative combinations of components. It should be understood that, although individual examples may be discussed herein, the present disclosure covers all combinations of the disclosed examples, including, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

For the sake of brevity, only certain ranges are explicitly disclosed herein. However, ranges from any lower limit may be combined with any upper limit to recite a range not explicitly recited, as well as ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A method comprising:

disposing a fluid sampling tool into a wellbore wherein the fluid sampling tool comprises:

at least one probe to fluidly connect the fluid sampling tool to a formation in the wellbore; and at least one passageway that passes through the at least one probe and into the fluid sampling tool;

drawing a formation fluid from a first sampling zone, as a fluid sample, through the at least one probe and through the at least one passageway; and analyzing the fluid sample in the fluid sampling tool for one or more ion components, wherein analyzing the fluid sample comprises:

using a downhole spectroscopy device; and using spectral deconvolution to quantify ions concentrations, wherein peak height, or Full Width Half Max (FWHM), or integrated area, or a combination thereof in combination with temperature and a model are used to quantify ion concentrations.

2. The method of claim 1, wherein the spectral deconvolution comprises Gaussian, Lorentzian or Voight Curve with Gaussian and Lorentzian addition.

3. The method of claim 2, wherein peak height, or Full Width Half Max (FWHM), or integrated area, or a combination thereof of at least one of the Gaussian and Lorentzian curves in combination with temperature and a model are used to quantify ion concentrations.

4. The method of claim 1, wherein analyzing the fluid sample comprises using a downhole optical sensor comprising multiple broad bandpass filters based on compressive sensing principle.

5. The method of claim 4, wherein the compressive sensing principle comprises a compressive sensing reconstruction algorithm and a fluid spectral database.

6. The method of claim 1, wherein the ion components are chloride ions.

7. The method of claim 1, wherein the ion components are either calcium ions, potassium ions, magnesium ions, or sulfate ions.

8. The method of claim 1, wherein the ion components are hydronium ions.

9. The method of claim 1, wherein the ion components are sodium ions.

10. The method of claim 1, wherein the ion components are lithium ions.

11. The method of claim 1, wherein the ion components are iron ions.

12. The method of claim 1, wherein the ion components are carbonate ions.

13. The method of claim 1, wherein the ion components are mercury ions.

14. The method of claim 1, further distinguishing fluid sample passing through the at least one passageway being contaminated by water-based mud filtrate through ions quantification.

15. The method of claim 1, further drawing a formation fluid from a second or more sampling zone and determining whether fluid sample in the at least one passageway being from the same formation fluid as the first sampling zone through ions quantification.

16. The method of claim 1, wherein the spectral deconvolution comprises Gaussian Curve.

17. A method of quantifying ions comprising:

pumping a fluid from a reservoir into a fluid sampling tool, wherein the fluid comprises ions;

measuring the fluid using an optical sensor comprising multiple broad bandpass filters;

using a compressive sensing reconstruction algorithm comprising first two principal components;

using a fluid spectral database;

using a clustering method for fluid identification; and using spectral deconvolution to quantify ions concentrations and determine reservoirs connectivity, wherein peak height, or Full Width Half Max (FWHM), or integrated area, or a combination thereof in combination with temperature and a model are used to quantify ion concentrations.

18. The method of claim 17, wherein the spectral deconvolution comprises Gaussian, Lorentzian or Voight Curve with Gaussian and Lorentzian addition.

19. The method of claim 18, wherein peak height, or Full Width Half Max (FWHM), or integrated area, or a combination thereof of at least one of the Gaussian and Lorentzian curves in combination with temperature and a model are used to quantify ion concentrations.

20. The method of claim 17, wherein quantifying ions comprises quantifying ions contribution to water chemistry in-situ.

\* \* \* \* \*